(12) United States Patent
Rosenbaum et al.

(10) Patent No.: US 10,751,085 B2
(45) Date of Patent: Aug. 25, 2020

(54) TROCAR ASSEMBLY WITH A MOVABLE CLEANING ELEMENT

(71) Applicant: CareFusion 2200, Inc., San Diego, CA (US)

(72) Inventors: Joanna L. Rosenbaum, Evanston, IL (US); Jeanny Chung, Deerfield, IL (US); Patrick Hubbard, Vernon Hills, IL (US); Joseph Prybell, Mundelein, IL (US); Corrie Threlkeld, Vernon Hills, IL (US); Sara Tillman, Vernon Hills, IL (US); Brandon Toth, Vernon Hills, IL (US); Andrew P. VanDeWeghe, Grayslake, IL (US); Thomas Wilschke, Chicago, IL (US); Jesse Charles Darley, Madison, WI (US); Christopher Alan Harris, Madison, WI (US); Curtis B. Irwin, Madison, WI (US); Stephen A. Latham, Sun Prairie, WI (US); Daniel J. Lee, Princeton Junction, NJ (US); Douglas Rodenkirch, Sun Prairie, WI (US); Jeffrey R. Staszak, Deerfield, WI (US)

(73) Assignee: CareFusion 2200, Inc., San Diego, CA (US)

( * ) Notice: Subject to any disclaimer, the term of this patent is extended or adjusted under 35 U.S.C. 154(b) by 0 days.

(21) Appl. No.: 15/993,276

(22) Filed: May 30, 2018

(65) Prior Publication Data
US 2018/0360490 A1 Dec. 20, 2018

Related U.S. Application Data

(60) Provisional application No. 62/513,270, filed on May 31, 2017, provisional application No. 62/513,278, filed on May 31, 2017.

(51) Int. Cl.
*A61B 17/34* (2006.01)
*A61B 1/12* (2006.01)
(Continued)

(52) U.S. Cl.
CPC ...... *A61B 17/3421* (2013.01); *A61B 1/00089* (2013.01); *A61B 1/00091* (2013.01);
(Continued)

(58) Field of Classification Search
CPC . A61B 17/3421; A61B 17/0218; A61B 17/34; A61B 17/3415; A61B 17/3474;
(Continued)

(56) References Cited

U.S. PATENT DOCUMENTS 5,274,874 A    1/1994  Cercone et al.
5,351,675 A   10/1994  Brodsky
(Continued)

FOREIGN PATENT DOCUMENTS

EP    2111782 A2   10/2009
EP    2111808 A2   10/2009
(Continued)

OTHER PUBLICATIONS

International Search Report and Written Opinion in Application No. PCT/US2018/020850, dated May 17, 2018, 12 pages.
(Continued)

*Primary Examiner* — Pedro Philogene
(74) *Attorney, Agent, or Firm* — Dinsmore & Shohl LLP

(57) ABSTRACT

A trocar assembly with an integrated scope-cleaning structure may have a proximal portion configured for accessibility by a user and a cannula extending distally from the proximal portion and configured to extend distally into a patient body, where the cannula is further configured to receive a distal end of a scope such that the scope can be maneuvered through the cannula to a location within the
(Continued)

patient body. A cleaning element may be included, where the proximal portion includes a housing, where the cleaning element is substantially located within the housing.

19 Claims, 19 Drawing Sheets

(51) Int. Cl.
    *A61B 1/313*     (2006.01)
    *A61B 90/70*     (2016.01)
    *A61B 17/02*     (2006.01)
    *A61B 1/00*     (2006.01)
    *A61B 17/00*     (2006.01)

(52) U.S. Cl.
    CPC ...... *A61B 1/00096* (2013.01); *A61B 1/00154* (2013.01); *A61B 1/126* (2013.01); *A61B 1/3132* (2013.01); *A61B 17/0218* (2013.01); *A61B 17/34* (2013.01); *A61B 17/3415* (2013.01); *A61B 17/3423* (2013.01); *A61B 90/70* (2016.02); *A61B 1/00135* (2013.01); *A61B 17/3474* (2013.01); *A61B 2017/00907* (2013.01); *A61B 2017/3437* (2013.01); *A61B 2090/701* (2016.02)

(58) Field of Classification Search
    CPC . A61B 90/70; A61B 1/00089; A61B 1/00091; A61B 1/00154; A61B 1/126; A61B 1/3132; A61B 1/00135; A61B 2017/00907; A61B 2017/3437; A61B 2090/701
    USPC ................ 600/101, 140, 144, 157, 201–210
    See application file for complete search history.

(56) References Cited

U.S. PATENT DOCUMENTS

| | | | |
|---|---|---|---|
| 5,365,267 A | | 11/1994 | Edwards |
| 5,382,297 A | | 1/1995 | Valentine et al. |
| 5,429,609 A | * | 7/1995 | Yoon .................. A61B 17/3417 604/167.03 |
| 5,518,502 A | | 5/1996 | Kaplan et al. |
| 5,549,543 A | | 8/1996 | Kim |
| 5,643,227 A | * | 7/1997 | Stevens ............. A61M 39/0606 604/167.02 |
| 5,651,757 A | | 7/1997 | Meckstroth |
| 5,842,971 A | * | 12/1998 | Yoon .................. A61B 17/3417 600/101 |
| 5,880,779 A | | 3/1999 | Rhynes |
| 5,910,106 A | | 6/1999 | Morgan et al. |
| 5,916,145 A | | 6/1999 | Chu et al. |
| 5,980,493 A | | 11/1999 | Smith et al. |
| 6,197,041 B1 | | 3/2001 | Shichman et al. |
| 6,319,266 B1 | | 11/2001 | Stellon et al. |
| 6,482,181 B1 | | 11/2002 | Racenet et al. |
| 6,497,716 B1 | | 12/2002 | Green et al. |
| 6,685,630 B2 | | 2/2004 | Sauer et al. |
| 6,976,957 B1 | | 12/2005 | Chin |
| 6,981,966 B2 | | 1/2006 | Green et al. |
| 7,025,747 B2 | | 4/2006 | Smith |
| 7,294,136 B2 | | 11/2007 | Dubrul et al. |
| 7,367,960 B2 | | 5/2008 | Stellon et al. |
| 7,390,315 B2 | | 6/2008 | Stellon et al. |
| 7,537,563 B2 | | 5/2009 | Temple |
| 7,691,089 B2 | | 4/2010 | Gresham |
| 7,771,384 B2 | | 8/2010 | Ravo |
| 7,811,225 B2 | | 10/2010 | Sauer et al. |
| 7,811,251 B2 | | 10/2010 | Wenchell et al. |
| 7,988,670 B2 | | 8/2011 | Smith |
| 8,070,730 B2 | | 12/2011 | Rockrohr |
| 8,092,423 B2 | | 1/2012 | Gresham |
| 8,123,682 B2 | | 2/2012 | Wenchell |
| 8,152,717 B2 | | 4/2012 | Gomez |
| 8,202,290 B2 | | 6/2012 | Smith |
| 8,206,411 B2 | | 6/2012 | Thompson et al. |
| 8,211,135 B2 | | 7/2012 | Heinrich et al. |
| 8,223,193 B2 | | 7/2012 | Zhao et al. |
| 8,241,251 B2 | | 8/2012 | Gresham |
| 8,257,253 B2 | | 9/2012 | Piskun |
| 8,257,254 B2 | | 9/2012 | Piskun |
| 8,257,315 B2 | | 9/2012 | Franer et al. |
| 8,267,896 B2 | | 9/2012 | Hartoumbekis |
| 8,394,018 B2 | | 3/2013 | Piskun |
| 8,449,460 B2 | | 5/2013 | Duke et al. |
| 8,458,971 B2 | | 7/2013 | Smith et al. |
| 8,491,545 B2 | | 7/2013 | Shelton, IV |
| 8,496,622 B2 | | 7/2013 | Shelton, IV |
| 8,535,220 B2 | | 9/2013 | Mondschein |
| 8,636,686 B2 | * | 1/2014 | Minnelli ............ A61B 1/00128 604/26 |
| D700,326 S | | 2/2014 | Minnelli et al. |
| 8,708,889 B2 | | 4/2014 | Feuer et al. |
| 8,726,037 B2 | | 5/2014 | Franer |
| 8,728,109 B2 | | 5/2014 | Piskun |
| 8,764,648 B2 | | 7/2014 | Piskun |
| 8,771,307 B2 | | 7/2014 | Franer |
| 8,870,747 B2 | | 10/2014 | Moreno, Jr. et al. |
| 8,911,463 B2 | | 12/2014 | Fischvogt |
| 8,932,249 B2 | | 1/2015 | Parihar et al. |
| 8,961,552 B2 | | 2/2015 | Fischvogt et al. |
| 8,968,250 B2 | | 3/2015 | McGinley et al. |
| 9,039,604 B2 | | 5/2015 | Yoshida |
| 9,078,562 B2 | | 7/2015 | Poll et al. |
| D736,926 S | | 8/2015 | Minnelli et al. |
| 9,211,059 B2 | | 12/2015 | Drach et al. |
| 9,265,899 B2 | | 2/2016 | Albrecht et al. |
| 9,289,115 B2 | | 3/2016 | Dang et al. |
| D753,303 S | | 4/2016 | Dannaher |
| 9,314,266 B2 | | 4/2016 | Kahle et al. |
| 9,314,267 B2 | | 4/2016 | Piskun et al. |
| 9,358,040 B2 | | 6/2016 | Kahle et al. |
| 2002/0022762 A1 | | 2/2002 | Beane et al. |
| 2002/0065450 A1 | | 5/2002 | Ogawa |
| 2003/0139649 A1 | | 7/2003 | Kasahara et al. |
| 2005/0043683 A1 | | 2/2005 | Ravo |
| 2006/0293559 A1 | | 12/2006 | Grice |
| 2008/0194915 A1 | | 8/2008 | Blackhurst et al. |
| 2008/0200765 A1 | | 8/2008 | Mondschein |
| 2008/0306335 A1 | | 12/2008 | Lau et al. |
| 2009/0112057 A1 | | 4/2009 | Kammer et al. |
| 2009/0240111 A1 | | 9/2009 | Kessler |
| 2009/0270686 A1 | | 10/2009 | Duke et al. |
| 2009/0270818 A1 | | 10/2009 | Duke |
| 2010/0012152 A1 | | 1/2010 | Hansen |
| 2010/0185139 A1 | * | 7/2010 | Stearns ............. A61B 17/3474 604/26 |
| 2011/0149057 A1 | | 6/2011 | Beck et al. |
| 2012/0101337 A1 | | 4/2012 | Clark et al. |
| 2012/0101338 A1 | | 4/2012 | O'Prey |
| 2012/0178995 A1 | | 7/2012 | Newton, IV |
| 2012/0187104 A1 | | 7/2012 | Heymann et al. |
| 2013/0041230 A1 | | 2/2013 | Hartoumbekis et al. |
| 2013/0053639 A1 | | 2/2013 | Ihde, II |
| 2013/0085329 A1 | | 4/2013 | Morrissette et al. |
| 2013/0102843 A1 | | 4/2013 | Feuer et al. |
| 2013/0150670 A1 | | 6/2013 | O'Prev et al. |
| 2014/0171739 A1 | | 6/2014 | Nguyen |
| 2014/0215736 A1 | | 8/2014 | Gomez |
| 2014/0235944 A1 | | 8/2014 | Feuer et al. |
| 2014/0249370 A1 | | 9/2014 | Hurst |
| 2015/0105626 A1 | | 4/2015 | Kleyman |
| 2015/0190041 A1 | | 7/2015 | Suehara et al. |
| 2015/0201826 A1 | | 7/2015 | Hsu et al. |
| 2015/0282695 A1 | | 10/2015 | Tay et al. |
| 2016/0015573 A1 | | 1/2016 | Ihde, III |
| 2016/0113484 A1 | | 4/2016 | Nakaguchi |
| 2016/0166135 A1 | | 6/2016 | Fiset |
| 2016/0317006 A1 | | 11/2016 | Gomez et al. |

(56) References Cited

U.S. PATENT DOCUMENTS

| | | |
|---|---|---|
| 2018/0035988 A1 | 2/2018 | Lau |
| 2019/0191982 A1* | 6/2019 | Fiset .................. A61B 1/126 |

FOREIGN PATENT DOCUMENTS

| | | |
|---|---|---|
| EP | 2113215 A1 | 11/2009 |
| EP | 2193742 A1 | 6/2010 |
| EP | 2238928 A1 | 10/2010 |
| EP | 2111782 B1 | 8/2016 |
| JP | 2007105314 A | 4/2007 |
| WO | 2008030256 A1 | 3/2008 |
| WO | WO2010/011563 A3 | 7/2009 |
| WO | WO2013/012790 A2 | 7/2012 |
| WO | WO2013/012790 A3 | 7/2012 |
| WO | WO2013/063153 A2 | 5/2013 |
| WO | WO2014/185334 A1 | 5/2014 |
| WO | 2018093817 A1 | 5/2018 |

OTHER PUBLICATIONS

International Search Report and Written Opinion in Application No. PCT/US2018/020856, dated May 17, 2018, 15 pages.

International Search Report and Written Opinion in Application No. PCT/US2018/020853, dated Jun. 18, 2018, 16 pages.

International Preliminary Report on Patentability dated Dec. 12, 2019 pertaining to International PCT Application PCT/US2018/035191.

International Preliminary Report on Patentability dated Dec. 12, 2019 pertaining to International PCT Application PCT/US2018/035206.

International Preliminary Report on Patentability dated Dec. 12, 2019 pertaining to International PCT Application PCT/US2018/035199.

* cited by examiner

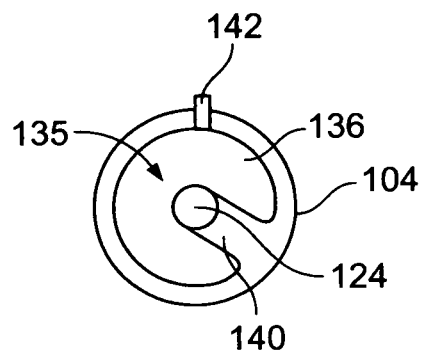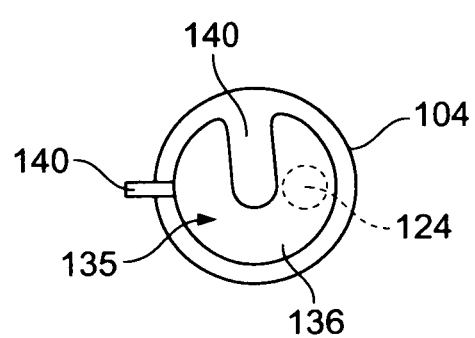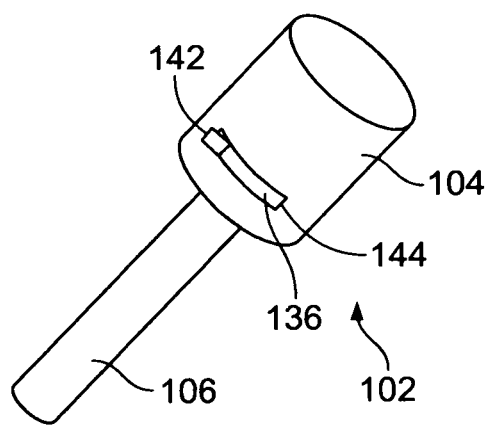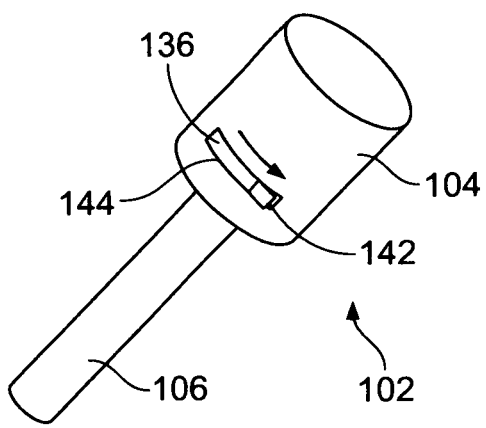
FIG. 3          FIG. 4

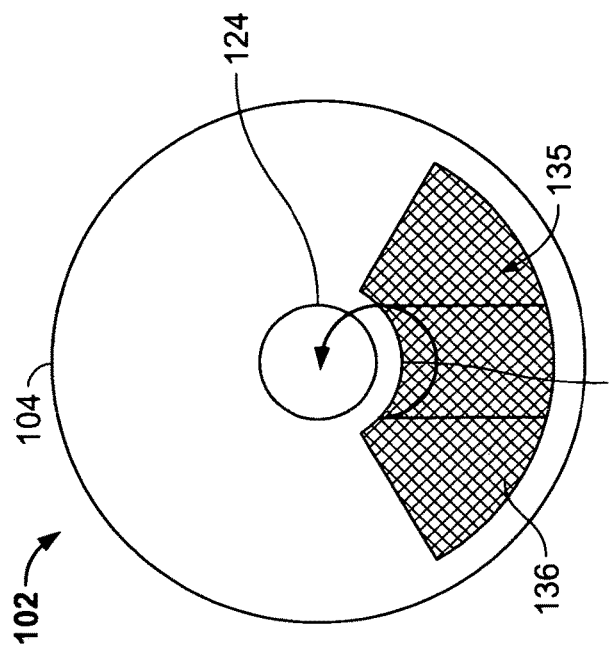
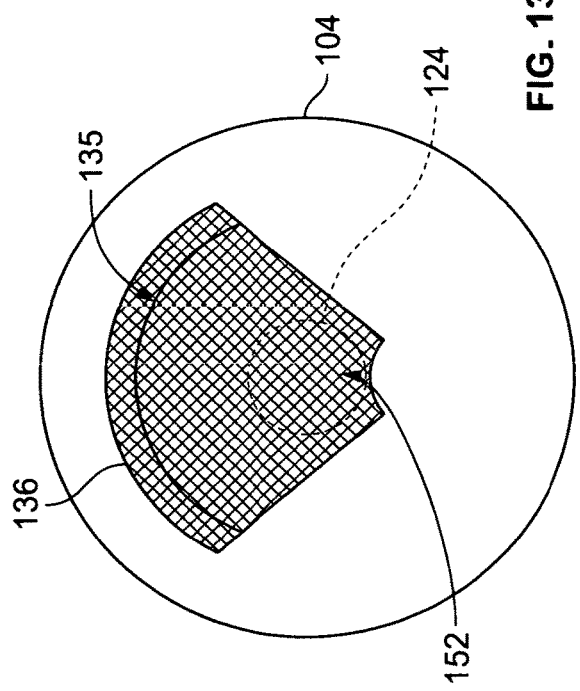
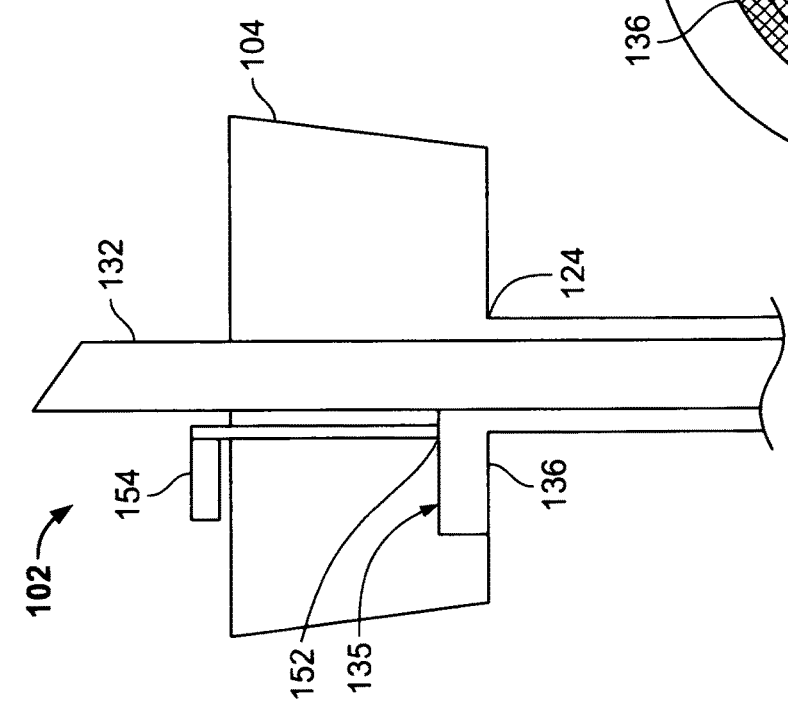

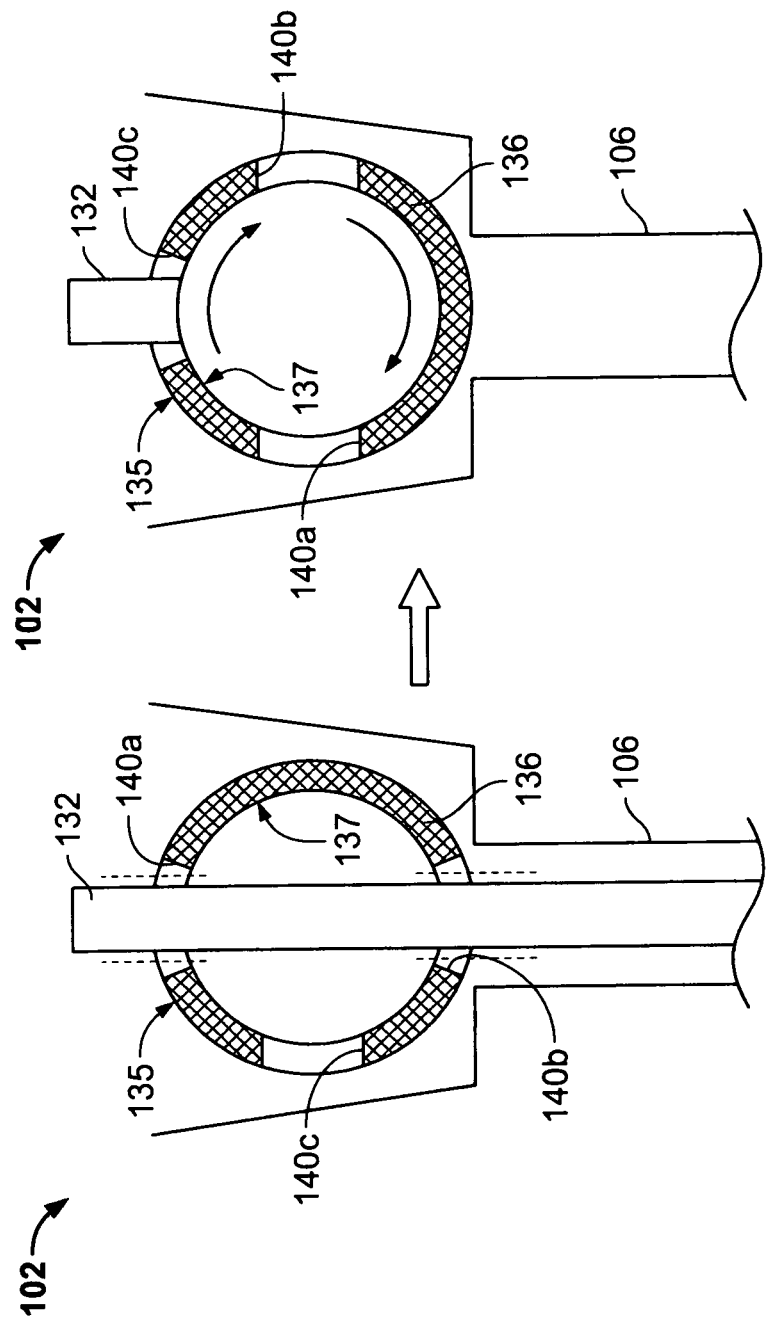

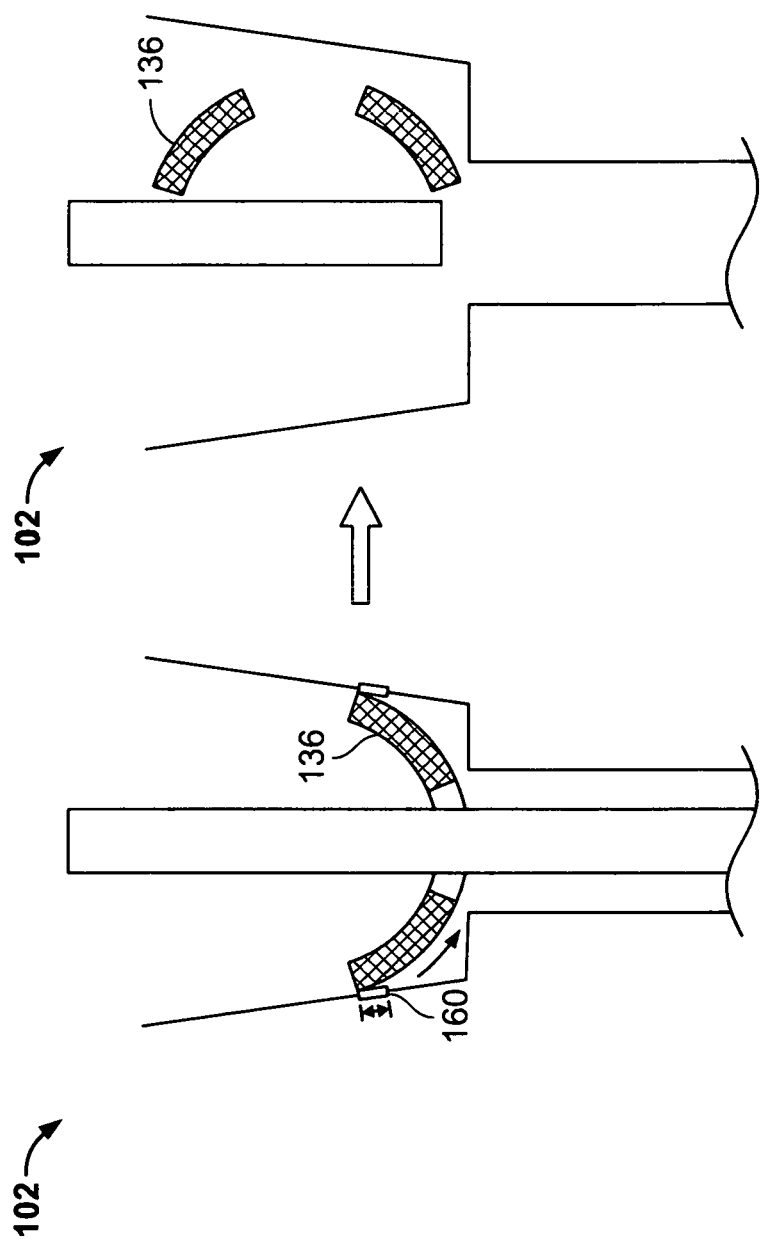

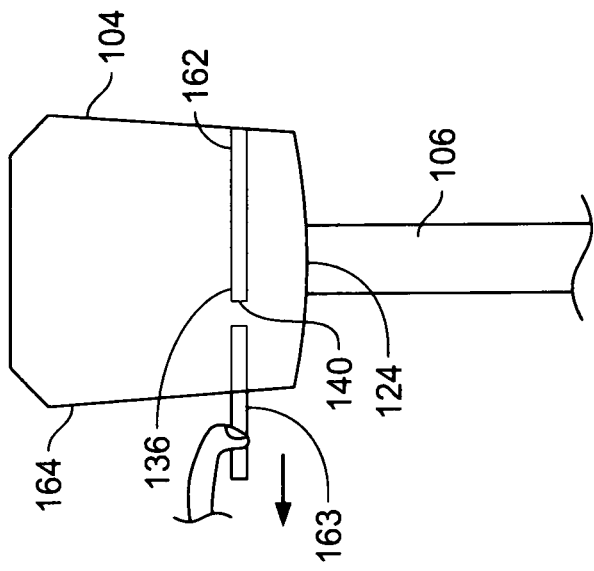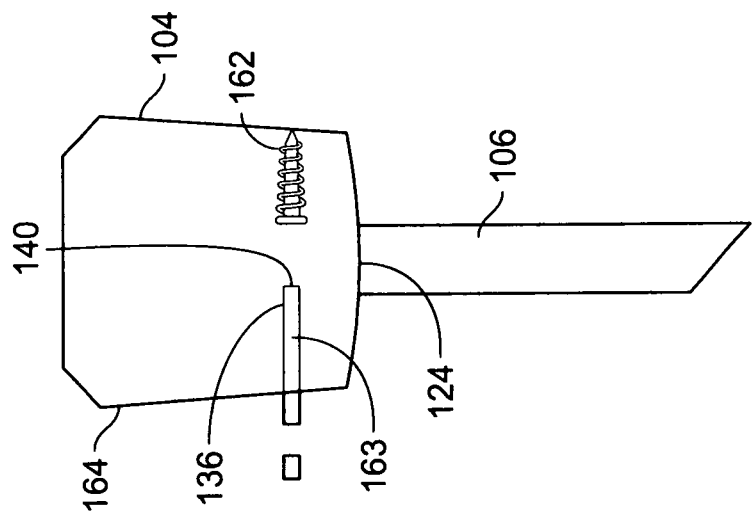

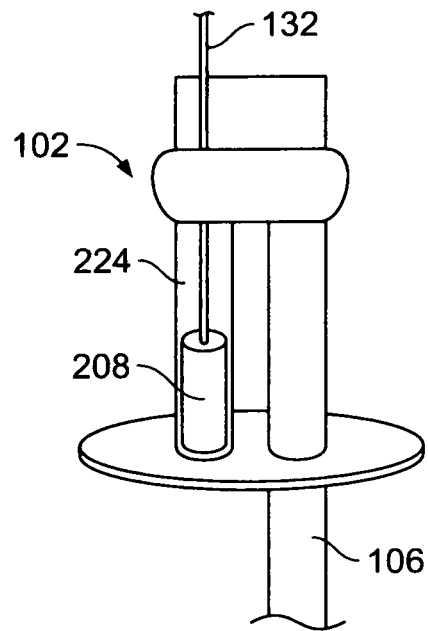
FIG. 33
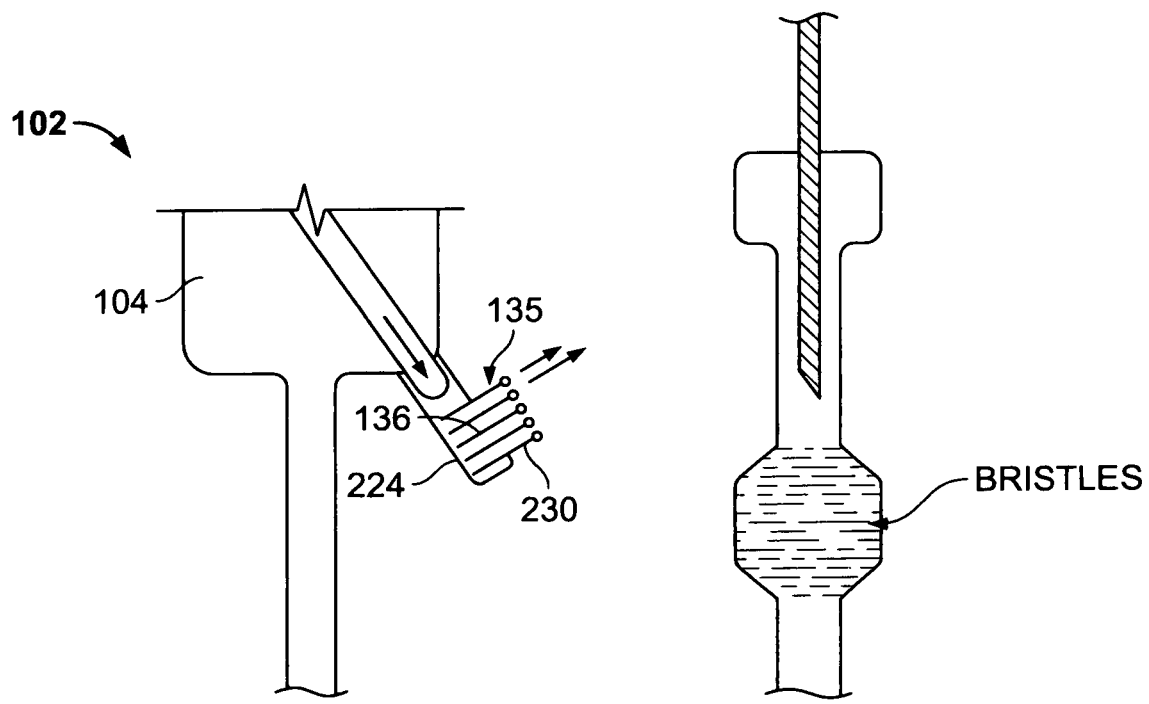
FIG. 34　　FIG. 35

TROCAR ASSEMBLY WITH A MOVABLE CLEANING ELEMENT

RELATED APPLICATIONS

This application claims the benefit of U.S. Provisional Application No. 62/513,270, filed May 31, 2017, and U.S. Provisional Application No. 62/513,278, filed May 31, 2017, each of which is herein incorporated by reference in its entirety. Further, each of the following applications, filed on Mar. 7, 2017, is herein incorporated by reference in its entirety: U.S. patent application Ser. No. 15/452,169, U.S. patent application Ser. No. 15/452,211, and U.S. patent application Ser. No. 15/452,246.

FIELD OF TECHNOLOGY

The present disclosure relates generally to scopes, such as laparoscopes, trocar assemblies, and related devices, and more specifically, to scopes for use with trocar assemblies, for example, which can be utilized in laparoscopic medical procedures.

BACKGROUND

Laparoscopic surgery is a minimally-invasive surgical technique typically performed with the assistance of one or more medical instruments inserted through a small incision in a patient's body. Laparoscopic surgery is often preferred to traditional and more invasive surgical procedures because of the reduced frequency and degree of certain postoperative side effects, such as postoperative pain, swelling, internal bleeding, and infection risk. The minimally-invasive nature of laparoscopic procedures may also result in decreased recovery times and shorter hospital stays.

Typical medical devices utilized during laparoscopic procedures have instruments mounted on an elongated metal or plastic body that are inserted into the patient's body and maneuvered to a target area within a body cavity (e.g., the abdominal, pelvic, thoracic, or chest cavity, where insufflation may be used to provide additional space in which to maneuver, which requires a fluid-patient barrier to maintain insufflation pressure in the cavity). One or more trocar assemblies are typically first inserted into the patient body at an incision site (for each), and the instruments access the patient body through the trocar assembly(ies).

Often, a medical device including a camera or other image-transmitting device is inserted through a trocar to transmit one or more images or a live video feed from within the body cavity to a medical professional (such as the surgeon). The device may be referred to as a scope or a laparoscope, and its transmission may guide the medical professional's actions during the laparoscopic procedure.

A problem typically experienced during laparoscopic procures involves a compromised image or video feed due to an obstructed lens of the laparoscope. This obstruction may be caused by condensation (e.g., fog) and/or debris such as bodily fluids or displaced tissue encountered by the lens during the procedure. Such obstruction is problematic because the lens of the laparoscope preferably remains contained in a pressurized and sterile environment (e.g., insufflated body cavity), and removing the lens from that environment for cleaning purposes may cause lengthy interruptions prolonging patient anesthesia and increasing a risk of compromised sterility.

SUMMARY

In one aspect, a trocar assembly with an integrated scope-cleaning structure including the following: a proximal portion configured for accessibility by a user; a cannula extending distally from the proximal portion and configured to extend distally into a patient body, where the cannula is further configured to receive a distal end of a scope such that the scope can be maneuvered through the cannula to a location within the patient body; and a cleaning element, where the proximal portion includes a housing, where the cleaning element is substantially located within the housing, and where the cleaning element includes an operation surface actuatable from outside of the housing and configured such that actuation of the operation surface moves the cleaning element within the housing.

In another aspect, a trocar assembly with an integrated scope-cleaning includes the following: a proximal portion; a cannula extending distally from the proximal portion and configured to extend distally into a patient body, where the cannula is further configured to receive a distal end of a scope such that the scope can be maneuvered through the cannula to a location within the patient body; and a cleaning element, where the proximal portion includes a housing, where the cleaning element is located within the housing, and where the cleaning element is coupled to an actuator that rotates the cleaning element within the housing when actuated.

In another aspect, a trocar assembly with an integrated scope-cleaning structure includes the following: a cannula configured to extend distally into a patient body, where the cannula is further configured to receive a distal end of the scope such that the scope can be maneuvered through the cannula to a location within the patient body; a flushing chamber positioned proximally of at least a portion of the cannula and configured to receive a distal end of a scope; and an inlet for supplying a fluid cleaning agent to the flushing chamber.

BRIEF DESCRIPTION OF THE DRAWINGS

FIG. 3-4 are illustrations showing various views of a trocar assembly with a rotatable cleaning element.

FIGS. 11-13 are illustrations showing various views of another embodiment of a trocar assembly with a rotatable cleaning element, where the cleaning element is mechanically coupled to a handle.

FIGS. 14-15 are illustrations showing two states of another embodiment of a trocar assembly with a rotatable cleaning element: an open state and a closed state.

FIGS. 16-17 are illustrations showing two states of another embodiment of a trocar assembly with a rotatable cleaning element.

FIGS. 18-19 are illustrations showing two states of a cleaning element having a collapsible portion and a second portion, where the second portion is accessible to a user outside a trocar housing.

FIG. 33 is an illustration showing another embodiment of a trocar assembly with an offshoot, where the offshoot is associated with a flushing chamber.

FIG. 34 is an illustration showing another embodiment of a trocar assembly with an offshoot, where the offshoot includes removable tabs.

FIGS. 35-38 are illustrations showing various embodiments of bristles included in a cannula of a trocar assembly for cleaning a scope.

DETAILED DESCRIPTION

Figure 1:
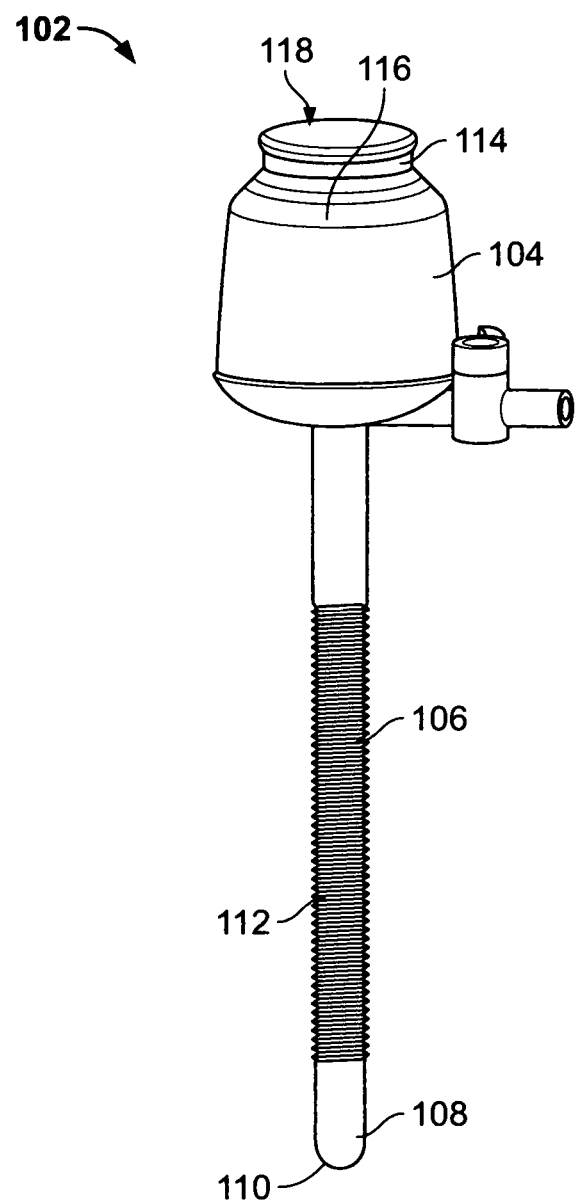
FIG. 1 is an illustration showing a front view of a trocar assembly.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings may or may not be to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry and/or governmental standards (e.g., ASTM, ANSI, IEEE, HIPAA, FDA standards) is defined as complying with the currently published standards as of the original filing date of this disclosure concerning the units, measurements, and testing criteria communicated by those standards unless expressly otherwise defined herein.

The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

FIG. 1 shows a trocar assembly 102 for use during a laparoscopic procedure. The trocar assembly 102 may include a housing 104 with a cannula 106 extending distally from the housing 104. The cannula 106 may include a distal end 108 for placement into a patient body during the laparoscopic procedure. The distal end 108 of the cannula 106 may include a beveled or sharpened end 110 to facilitate entry of the cannula 106 into the patient body. An obturator may additionally or alternatively be included. The cannula 106 may include certain surface characteristics, such as threads or ridges 112, to enhance the stability of the trocar assembly 102 when inserted into a body incision. In some embodiments, a removable bayonet fitting 114 or other suitable securement mechanism may be placed on a proximal side 116 of the housing 104 during deployment of the trocar assembly 102. The bayonet fitting 114 may be configured to secure an obturator to the housing 104 and may provide a surface 118 for receiving an input force from a medical professional intended to direct the cannula 106 into the patient body, for example. The bayonet fitting 114 may be removed once the trocar assembly 102 is deployed.

Figure 2:
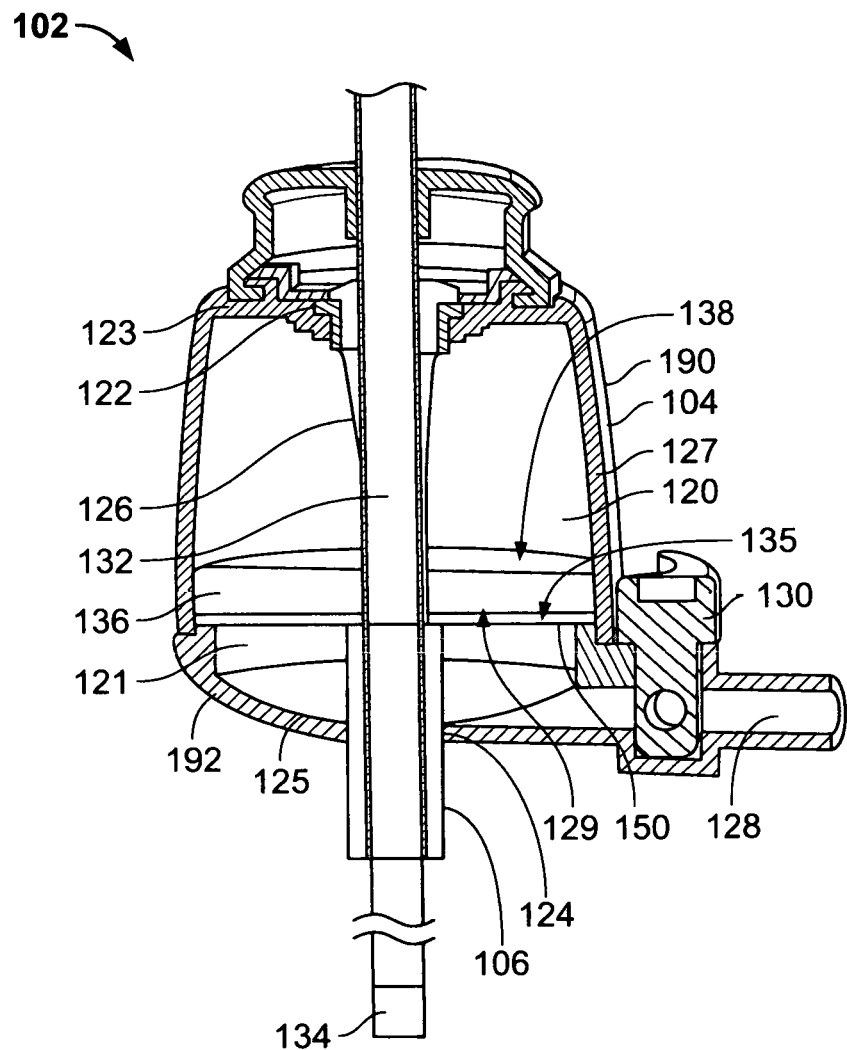
FIG. 2 is an illustration showing a section view of the trocar assembly of FIG. 1.

FIG. 2 shows a section view of the trocar assembly 102 of FIG. 1. As shown, the cannula 106 may be in fluid communication with a chamber 120 formed by the housing 104. The chamber 120 may be defined by a proximal or top wall 123, a distal or bottom wall 125, and a generally cylindrical side wall 127 extending from the top wall 123 to the bottom wall 125 and defining inner and outer chamber perimeters (i.e., circumferences, when the chamber is rounded but otherwise applicable to any geometry). The chamber 120 may have a proximal opening 122 configured to receive medical devices used during laparoscopic surgery, including but not limited to graspers, dissectors, needles, scissors, clamps, electrodes, forceps, a camera or laparoscope (a "scope"), etc. The proximal opening 122 may be located in a top wall 123 of the housing 104. A valve 126 may be located in the proximal opening 122 and may form a seal or fluid barrier between the chamber 120 and an external environment (e.g., the ambient room environment). Alternatively or in addition, the valve 126 may be located in another location (such as at the distal opening 124). It may be advantageous for at least one valve 126 to be located at the proximal opening 122 such that a lens of a scope does not have to pass through the valve 126 prior to cleaning, thereby reducing or eliminating the chance of materials from the valve 126 dirtying the scope's lens after cleaning. The inner and outer chamber perimeters each is greater than an outer perimeter of the cannula 106.

The chamber 120 may be subjected to a continuous sterile and pressurized environment that extends through the cannula 106 and to the body cavity (herein referred to as the "internal environment" even though the continuous region may extend external of the patient body wall, e.g., within trocar assembly 102). This may be advantageous if maintaining insufflation of the body cavity is desired during all operation—including cleaning—of a trans-trocar-located scope or other device. Further, the controlled environment of the chamber 120 may reduce fogging of a scope by eliminating or reducing temperature changes and/or changes in humidity.

The valve 126 (which may include more than one valve) may include a particular structure that allows certain medical devices to pass through the proximal opening 122 and into the chamber while maintaining the seal or fluid barrier. For example, the valve 126 may include the depicted duckbill seal, an annular seal structure, or both, but other suitable structures may additionally or alternatively be included. The valve 126 may be formed with a compliant material such that it expands or contracts as necessary for compatibility with scopes of different sizes. For example, on the Shore Hardness Scale, the valve 126 may be formed of a material with a hardness between about Shore A 20 to about Shore A 80, such as from about Shore A 30 to about Shore A 60.

An insufflation inlet 128 may communicate with the chamber and may be configured to control the pressure and other characteristics (e.g., temperature, composition of the atmosphere), which may be advantageous for providing precise control of insufflation of a body cavity during the laparoscopic procedure. The insufflation inlet 128 may include an insufflation valve 130 and may be in fluid communication with a pump or other suitable pressure source. As shown, the insufflation inlet 128 may communicate with a distal chamber portion 121 (which is a portion of the chamber 120) that is separated from the remainder of the chamber 120 by a divider 150, and the cleaning element 136 may be located on a proximal face of the divider 150, as shown. Advantageously, the flow of gasses or other contents received into the chamber 120 through the insufflation inlet 128 may be introduced in a manner such that the effect of the flow across cleaning element 136 is reduced or eliminated. For example, when the cleaning element 136 (which is described in detail below) is wetted with a cleaning fluid, concerns of increased evaporation due to fluid flow over the cleaning element 136 may be alleviated.

The trocar assembly 102 may provide an entry or point of access into the body for a scope 132. In non-limiting embodiments, the scope 132 may include a commercially-available rigid laparoscope with a 5 mm or a 10 mm diameter (or any other suitable diameter) with either a non-angled lens or an angled lens, which may be angled at 30 degrees, 45 degrees, 50 degrees, etc. with respect to the longitudinal axis of the scope 132. At least a distal end 134 of the scope 132 may include one or more elements designed to magnify, reflect, illuminate, and/or capture images of internal body areas under treatment, and then transmit those images back to the medical professional controlling the procedure (herein referred to as a "viewing element"). The scope 132 may be inserted into proximal opening 122 of the chamber 120, may extend through the chamber 120, and may extend through into the cannula 106 through a distal opening 124 in the bottom wall 125 of the chamber 120, where the distal opening 124 is in fluid and mechanical communication with the cannula 106. The scope 132 may further extend distally to the cannula's distal end 108 (shown in FIG. 1) and into the body cavity. In some embodiments, a sleeve (not shown, but readily understood as a lining layer) may be located within the cannula 106, and the scope 132 may pass through the sleeve. Once deployed, the scope 132 may be manipulated by the medical professional moving it distally/proximally, angling it, and/or by rotating it into a particular orientation. Typically, during laparoscopic procedures, scopes can become obstructed when debris (e.g., condensation, displaced tissue, bodily fluids) are encountered and accumulate on a lens of the scope, which may compromise the image or video feed provided to the medical professional.

As shown in FIG. 2, the trocar assembly 102 may include the cleaning element 136 forming a surface 138 at a location within the internal environment. The housing 104 may include a cleaning element receiving surface 135 configured (e.g., sized and shaped) to receive, and attach to, the cleaning element 136. The cleaning element may have a surface (such as the bottom surface 129) configured to secure to the cleaning element receiving surface 135. For example, the bottom surface 129 may have an adhesive or other tacky/sticky substance to adhere to the cleaning element receiving surface 135, but additional and/or alternative securement devices are contemplated. The surface 138 of the cleaning element 136 may facilitate removal of obstructions from the scope 132 without necessitating removal of the scope 132 from the internal environment. Advantageously, lengthy interruptions (and therefore increased surgical and anesthesia time) due to removing and/or replacing an obstructed scope may be reduced or eliminated. Further, the distal end of the scope 132 may remain in the sterile internal environment during cleaning, which may advantageously alleviate concerns related to loss of sterility within the internal environment due to the removal and re-entry of the scope 132 one or more times for cleaning purposes. Keeping the scope 132 within the internal environment may also reduce or eliminate debris in the form of fogging or condensation caused by exposure to pressure and/or temperature changes when switching between environments. It should also be understood that certain advantages of the present embodiments are generally described as relating to a scope for explanation purposes and may also extend to other types of instruments used during surgical procedures, and therefore "scope" should be understood as including any suitable medical device used during laparoscopic surgery when described in the context of the present embodiments, unless clearly excluded.

The cleaning element 136 may incorporate any suitable structures, materials, and/or cleaning solutions for removing obstructions from the scope 132. The cleaning element may have a unitary construction, or alternatively may have multiple surfaces or layers with different cleaning characteristics or properties for facilitating multiple treatments. For example, it is contemplated that the cleaning element 136 may have a first region with an abrasive surface for breaking up potential obstructions, a second region including a liquid, a gel, or other material for dissolving or washing away the obstructions, and a third region with an absorbent or adsorbent surface for removing any remaining residue.

The cleaning element 136 may include any suitable cleaning structures or materials, such as sponges, foams (e.g., reticulated or non-reticulated foamed plastic polymers forming open-cell, semi-open cell, or closed-cell foam structures), fibrous materials (e.g., materials with natural (e.g., cellulosic) and/or synthetic fibers), microfiber or wipe materials (e.g., polyethers, polyamides, polyesters, and/or blends of each in a woven or non-woven construction with split or non-split fibers), hydrophilic or hydrophobic materials, fluids, gases, bristles, films, etc. The structures and/or materials of the cleaning element 136 may include hydrophobic properties to assist in absorbing and wicking of various bodily fluids and/or lipophilic characteristics for increased absorption of oils or fats. The cleaning element 136 may be capable of absorbing at least 5 times its original weight of fluids, such as about 15 times its original weight (or more). When the cleaning element 136 includes pores, consistent or variable pore sizes may be consistently or randomly dispersed (or layered) in certain configurations for suitable absorption properties (for example, the cleaning element 136 may include a micro-porous foam with about 4 pores per inch to about 100 pores per inch). The cleaning element 136 may have a firmness/compliance of about 2 lbs/50 in2 to about 80 lbs/50 in2, and preferably about 6 lbs/50 in2 to about 45 lbs/50 in2 (when tested at 25% deflection on a 20 inch by 20 inch by 4 inch specimen). The material(s) of the cleaning element 136 may be formed of a material suitable for use in a medical device (e.g., with suitable biocompatibility, non-linting/no particulate, tear resistance, sterilization or other chemical/solvent compatibility, and radiation stability).

The cleaning element 136 may be multi-layered in some embodiments. For example, a first layer may be configured to absorb a fluid obstruction located on the scope 132, and a second layer may be configured to retain or discard that fluid. In some embodiments, the first layer may include an open-cell foam with relatively low density (such as polyurethane or silicone foam) that may be used to effectively and quickly absorb (or wick, etc.) the obstructing fluid, and the second layer may include higher-density foam for effectively retaining the fluid. The second layer may be located beneath (e.g., covered by) the first layer, for example. Fibrous materials such as terrycloth and microfiber cloths may additionally or alternatively be used and may be advantageous for providing a streak-free lens surface when wiped against the scope 132. The solid materials of the cleaning element 136 may be combined or "wetted" with a cleaning fluid, such as an anti-fog fluid, sterile water, saline, a detergent, etc., which may facilitate the removal of fatty smudges and dried-on debris.

Referring to the trocar assembly 102 of FIG. 2, in the event the medical professional's visibility becomes compromised due to obstruction of the scope 132 during surgery, the scope 132 may be retracted proximally such that the distal end of the scope 132 is located within the chamber 120. The distal end 134 (or other location) may then be wiped or swept by pressing and/or rubbing the distal end 134 of the scope 132 on the cleaning element 136 to remove obstructions. As explained above, this cleaning procedure may advantageously be completed without removing the scope 132 from the internal environment in the trocar assembly 102. In some embodiment, the housing 104 may be formed of a transparent or translucent material such that a user has a visual perspective of the cleaning element 136, the scope 132, and other objects in the chamber 120 during the cleaning procedure. Similarly, the cannula 106 may be formed of a transparent or translucent material. When the scope 132 is located in the trocar assembly 102, the scope 132 (which often includes a light) may illuminate the chamber 120 to increase visibility, even if the housing 104 is not fully transparent. While the housing 104 may be fully formed of a transparent or translucent material, the housing 104 may alternatively include an opaque material and also include at least one viewport formed of transparent or translucent material.

In some embodiments, the cleaning element 136 may be selectable, removable, and/or replaceable. Thus, the trocar assembly 102 may be capable of allowing access into the chamber 120 (e.g., in an operating room prior to a surgery) such that a medical professional can select an appropriate version of the cleaning element 136 and then use that cleaning element 136 with the trocar assembly 102 during the procedure. The access may be provided by separating an upper portion 190 of the housing from a lower portion 192 of the housing, for example. The cleaning element 136 may additionally or alternatively be replaced during a medical procedure (e.g., if it becomes soiled), and/or may be replaced between medical procedures during reprocessing of the trocar assembly 102 if the trocar assembly 102 is reusable.

After completion of the cleaning procedure, the distal end 134 of the scope 132 may be again advanced through the cannula 106 and out beyond the cannula distal end to restore the image or video feed provided by the scope. Those of skill in the art will appreciate that existing scopes and potential scope designs include at least one non-longitudinal, distal-end-facing surface of the distal end 134 that may be generally or exactly perpendicular to the longitudinal axis of the scope 132, or which distal-facing surface may be configured at a non-perpendicular angle relative to the longitudinal axis (e.g., 30 degrees off-perpendicular, 45 degrees off-perpendicular). It is further contemplated that the distal-facing surface of the scope 132 may be flat/planar, concave, or convex relative to the major plane of that face. The term "non-longitudinal, distal-end-facing surface" is meant to include the operative end face(s) of a scope in distinction from the longitudinal lateral sides of the scope, which will generally be columnar or cylindrical. Thus, as described in more detail below, the surface characteristics of the cleaning element 136 may be shaped or otherwise configured for compatibility with a variety of distal-facing surfaces of the scope 132.

FIGS. 3 and 4 show an embodiment of a trocar assembly 102 with a cleaning element 136 configured to rotate for selective alignment with a distal opening 124 (where each of FIGS. 3-4 shows an outer perspective view and also a top internal view). The cleaning element 136 may include any compatible feature described in the description above (e.g., features for cleaning a scope). The cleaning element 136 may have a generally horseshoe shape or another suitable shape such that, when in a first state (shown in FIG. 3), a gap 140 of the cleaning element 136 is aligned with the distal opening 124 of the housing 104, where the distal opening 124 provides a path for mechanical communication with/into a cannula 106. In a second state (shown in FIG. 4), a portion of the cleaning surface 135 of the cleaning element 136 may at least partially block the distal opening 124. To clean a scope (not shown), a medical professional may move the cleaning element 136 from the depicted first state in FIG. 3 to the depicted second state of FIG. 4 such that, when the scope is moved distally towards the distal opening 124, it contacts the cleaning element 136. The cleaning element 136 may be moved through actuation of a lever 142 or other suitable operation surface (where "operation surface" herein means any surface that is actuatable by a user or through a programmed device to move the cleaning element, include levers, spring interfaces, handles, pull-strings, finger ports, rotatable pins, bristles, motor interfaces, insufflation-control interfaces, valves, and all other suitable actuators and interfaces). The lever 142 may extend through an opening 144 through the housing 104 such that it is accessible to a medical professional. A seal (e.g., a cover for preventing fluid flow or another suitable device) may be placed over the opening 144 and/or the lever 142 to retain a barrier between internally and externally of the housing 104 (e.g., to maintain insufflation pressure in the cavity). Advantageously, this embodiment may provide a quick and efficient mechanism for allowing a medical professional to retract a scope proximally through the distal opening 124, switch the cleaning element 136 from the first state to the second state for cleaning (which may include reciprocating or other movement of the cleaning element while it is in contact with a surface of the scope), and then move the cleaning element 136 back to the first state such that the scope can again deployed through the cannula 106.

Figure 5:
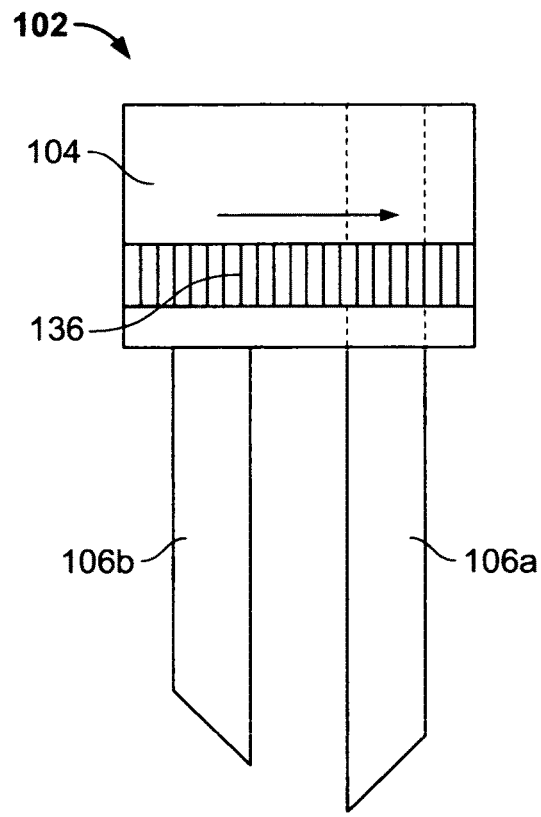
FIGS. 5-7 are illustrations showing various views of another embodiment of a trocar assembly with a rotatable cleaning element.
Figure 6:
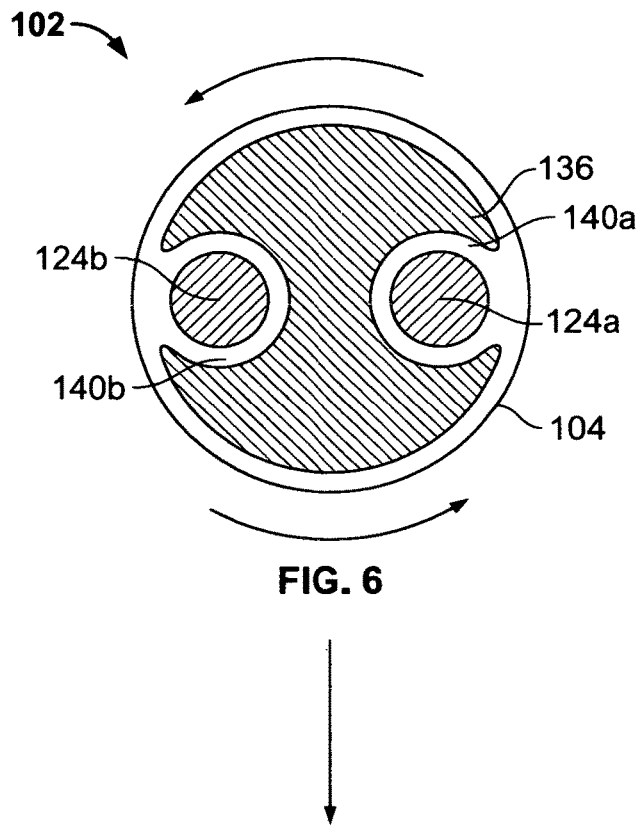
Figure 7:
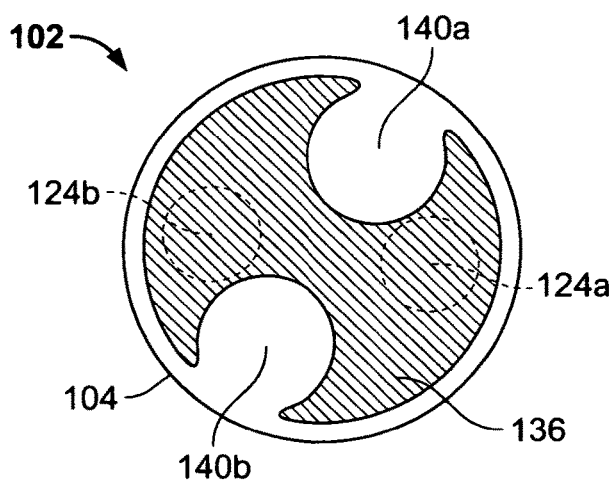

FIG. 5-7 show various views of a trocar assembly 102 with a cleaning element 136 configured to rotate for selective alignment with a first opening 124a. The embodiment of FIGS. 5-7 is similar to the embodiment of FIGS. 4-5, but the cleaning element 136 of FIGS. 5-7 is shaped for alignment with more than one opening. As shown, the first gap 140a may selectively align with the first opening 124a, and a second gap 140b may selectively align with a second opening 124b. Advantageously, the cleaning element 136 may be used in an embodiment where more than one cannula 106a, 106b extends from a housing 104 of the trocar assembly 102 (e.g., where each cannula is configured for a different function and/or a different scope). Alternatively, the first opening 124a may be associated with a passage to a cannula, while the second opening 124b may be a passage to something else. For example, the second opening 124b may lead to a rinsing or cleaning chamber (e.g., as shown in FIG. 33). While first gap 140a and the second gap 140b are depicted as being simultaneously aligned with the first opening 124a and the second opening 124b (respectively), it is also contemplated that only one of the first gap 140a and the second gap 140b may align with one opening at a time (e.g., one may be aligned when the other is offset). It is further contemplated that the first gap 140a may align with the second opening 124b and the second gap 140b may align with the first opening 124a. More (or fewer) than two gaps may be included for communication with more (or fewer) than two openings, and the number of gaps of the cleaning element 136 may be less than, equal to, or greater than the number of openings. Further, the so-called "gaps" do not necessarily have to extend to an edge of the cleaning element 136, but rather could be formed by openings that are completely surrounded.

Figure 8:
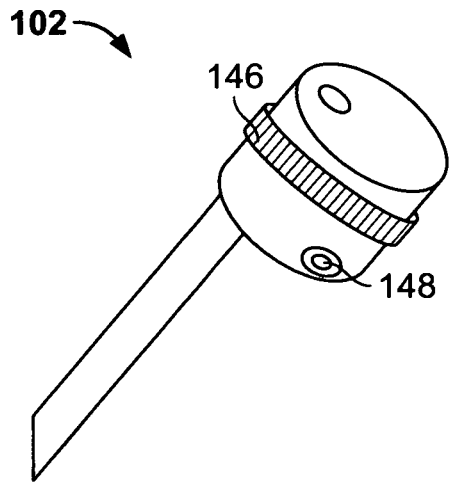
FIGS. 8-10 are illustrations showing various views of another embodiment of a trocar assembly with a rotatable cleaning element, where the rotatable cleaning element is coupled to a torsion spring.
Figure 9:
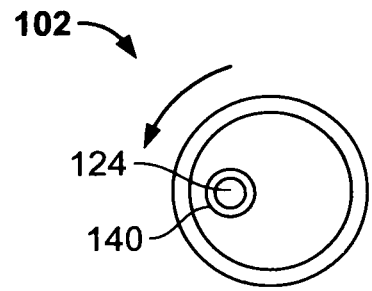
Figure 10:
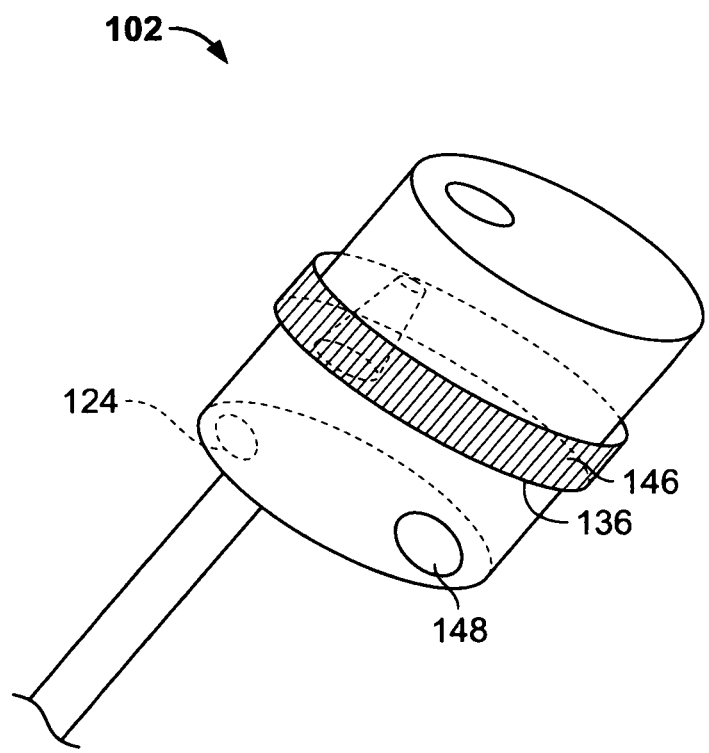

FIGS. 8-10 show an embodiment of trocar assembly 102 with a cleaning element 136 that is rotatable similar to the embodiments described above, but where the force for rotating the cleaning element 136 is provided by a spring 146 or another source of stored energy (rather than by manual manipulation by a user, where the spring or other source of stored energy is illustrated here only in simplified/diagrammatic fashion but will be understood by those of skill in the art to have many different embodiments). The spring 146 may be a torsion spring that can be wound either during manufacturing of the trocar assembly 102 or by a user prior to, or during, a medical procedure. The trocar assembly 102 may include an actuation control button 148 or another device for initiating movement (e.g., rotation) of the cleaning element 136. The actuation control button 148 may be mechanically coupled to a locking mechanism locking the cleaning element 136 in place such that, when pressed, the actuation control button 148 releases the locking mechanism and allows the spring 146 to rotate or otherwise move the cleaning element 136. In some embodiments, actuation may cause the gap 140 to align with the opening 124. Alternatively, the gap 140 may be initially aligned with the opening 124 and may misalign with the opening 124 when the actuation control button 148 is triggered. It is contemplated that the spring 146 may have enough stored energy such that multiple actuations are possible without multiple windings. For example, a first actuation may cause the gap 140 to rotate such that it is aligned with the opening 124, and a second actuation (without intervening winding) may cause the gap 140 to rotate out of alignment with the opening 124. Any number of consecutive actuations without intervening winding is contemplated.

FIGS. 11-13 show an embodiment of a trocar assembly 102 with a cleaning element 136 that is rotatable about a pivot point 152. Specifically as shown in FIG. 12, the cleaning element 136 may be at least partially, or fully (as shown), offset from the distal opening 124 such that access is not restricted in a first state, and thus a scope may have access to a cannula 106 (FIG. 11) extending from the distal opening 124. A handle 154 (shown in FIG. 11) may couple to (e.g., in a fixed manner) the cleaning element 136 (potentially at the pivot point 152), and may be accessible to a user from outside of the housing 104. The shape and the position of the cleaning element 136, along with the position of the pivot point 152, may be such that the cleaning surface 135 of the cleaning element 136 at least partially covers the opening 124 when the cleaning element 136 is rotated a selected amount (such as about 180 degrees in this particular embodiment. While any suitable shape is contemplated, the cleaning element 136 includes a portion of (e.g., an arc of) a disk in the embodiment of FIGS. 11-13, and the pivot point 152 is located adjacent to the distal opening 124 within the housing 104. When it is desirable to block the opening for cleaning a distal end of a scope on the cleaning surface (as described above), a medical professional may rotate the cleaning element 136 by gripping and moving the handle 154 such that the cleaning element 136 moves such that it covers the distal opening 124, as shown in FIG. 13, thus providing a state that is advantageous for simplicity of cleaning the scope 132. Like certain embodiments described above, it is contemplated that the trocar assembly 102 may include a stored energy source for providing the rotation of the cleaning element 136, which may be used in additional to, or as an alternative to, the handle 154.

FIGS. 14-15 and 16-17 show two other embodiments of a trocar assembly 102 having a rotatable cleaning element 136. For example, referring to FIGS. 14-15, a cleaning element 136 may be substantially formed as a sphere, cylinder, or other shape with a circular cross-section, where the axis through a circular cross-section is perpendicular with respect to the longitudinal direction of the cannula 106. As shown, the cleaning element 136 may include gaps 140a, 140b such that the scope 132 can pass all the way through the cleaning element 136 when the cleaning element 136 is in a certain position (such as the position depicted in FIG. 14). When the cleaning element is rotated (e.g., into the position shown in FIG. 15), the cleaning element 136 may block access to the cannula 106, and thus a scope moving towards the cleaning element 136 will make contact with an outer cleaning surface 135. In some embodiments, it is contemplated that an inner surface 137 of the cleaning element 136 may be associated with a different cleaning step than an outer surface 135 of the cleaning element 136. For example, the inner surface 137 may include a particular chemical cleaning agent, while the outer surface 135 does not (or includes a different agent) such that the inner surface 137 is associated with "wet" cleaning while the outer surface 135 is primarily associated with wiping or drying the scope 132. Optionally, an additional opening or gap (e.g., a third gap 140c) may be included through the outer surface 135 of the cleaning element 136 to provide access to the interior of the cleaning element 136, including portions of the inner surface 137. The cleaning element 136 may lack another opening situated across the cleaning element 136 from the third opening such that the scope does not travel through and out of the cleaning element 136 when the third opening is in use, which may be advantageous when contact between the scope 132 and the inner surface 137 of the cleaning element is intended.

The cleaning element 136 shown in FIGS. 16-17 is similar to the cleaning element 136 of FIGS. 14-15, and has many of the same functions and advantages, but it is shaped as only an arc or other portion of a cylinder or sphere. An actuator 160, shown in FIG. 14, may be coupled to the cleaning element 136 in any suitable manner and may be configured to cause movement of the cleaning element 136 between states. Any suitable actuator may be used, and particular examples are described below.

FIGS. 18-19 show a cleaning element 136 with a collapsible portion 162 located in a housing 104. As shown in FIG. 18, the collapsible portion 162 may include a "scrunched" structure, in particular a partially or fully-folded structure that remains offset with respect to the opening 124 leading to the cannula 106 when in a default state. An opening or gap 140 of the cleaning element 136 may be aligned with the opening 124 when in this default state. In certain embodiments, the collapsible portion 162 may include a spring-like resiliency such that it remains in the collapsed default state when no external force is applied. To extend the collapsible portion 162 over the opening 124, a user (and/or mechanical device) may apply a tension force to a second portion 163 of the cleaning element 136. The second portion 163 of the cleaning element 136 may transfer said force to the collapsible portion 162 such that the collapsible portion 162 expands into an extended cleaning state as shown in FIG. 19. The second portion 163 of the cleaning element 136 may extend through a wall 164 of the housing 104 such that it is accessible by a user, and thus the wall 164 may include a corresponding opening (and potentially a seal for maintaining a barrier between external and internal of the housing 104). In certain embodiments, the second portion 163 may include a string or other device that is configured to be gripped by the user, but that is not large enough to substantially block the opening 124 when the cleaning element 136 is in the default state of FIG. 18.

Figure 21:
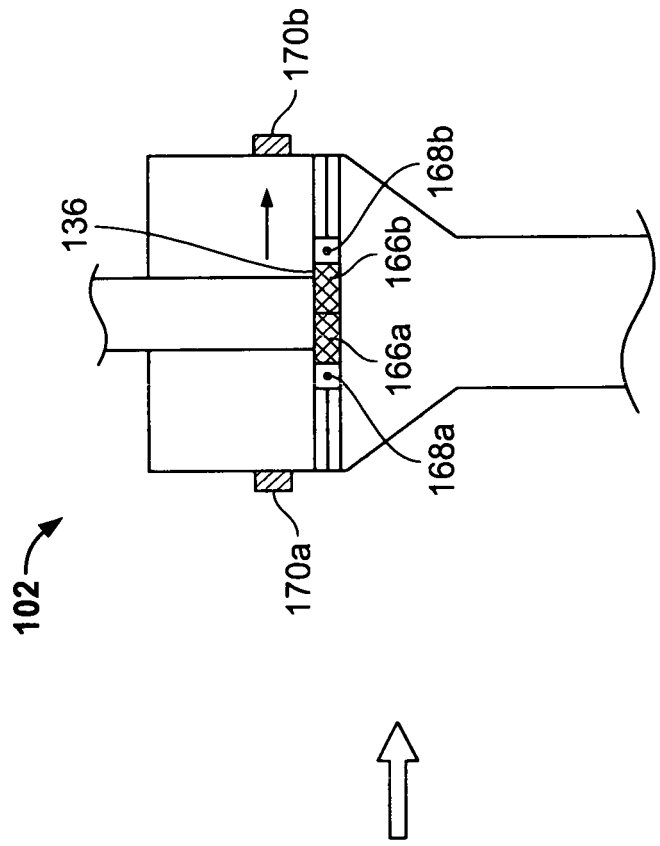
FIGS. 20-21 are illustrations showing two states of a trocar assembly with a cleaning element having two pivotable doors.
Figure 20:
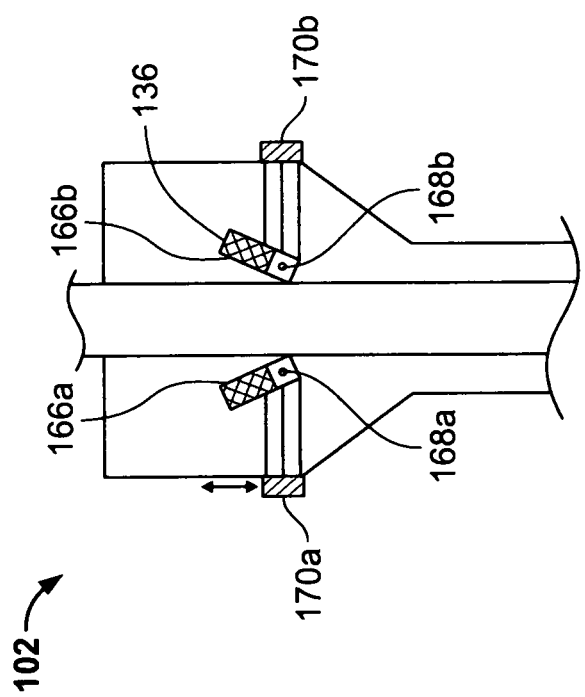

FIGS. 20-21 show a cleaning element 136 that includes two movable doors: a first door 166a and a second door 166b. More or less than two doors can be included. As shown, the first door 166a is pivotable about a first hinge 168a, and the second door 166b is pivotable about a second hinge 168b. The first and second doors 166 may be operable independently or collectively. In the depicted embodiment, a first lever 170a is mechanically coupled to the first door 166a (e.g., via a wire or another suitable device), and movement of the first lever 170a (e.g., from the position of FIG. 20 to the position of FIG. 21) causes movement of the first door 166a by way of transferring force through the wire and forcing the first door 166a to pivot about the first hinge 168a. The second lever 170b and second door 166b may operate in a similar or identical manner (though it is also contemplated that only one lever, or other actuator, could operate both doors simultaneously). Optionally, the first door 166a and/or the second door 166b may be associated with springs such that they are open when in a default state and must be forced closed prior to a cleaning step. Like the cleaning elements 136 described elsewhere in this description, the doors 166 may have cleaning surfaces configured for scope cleaning that block access to the cannula in a closed state (of FIG. 21).

Figure 22:
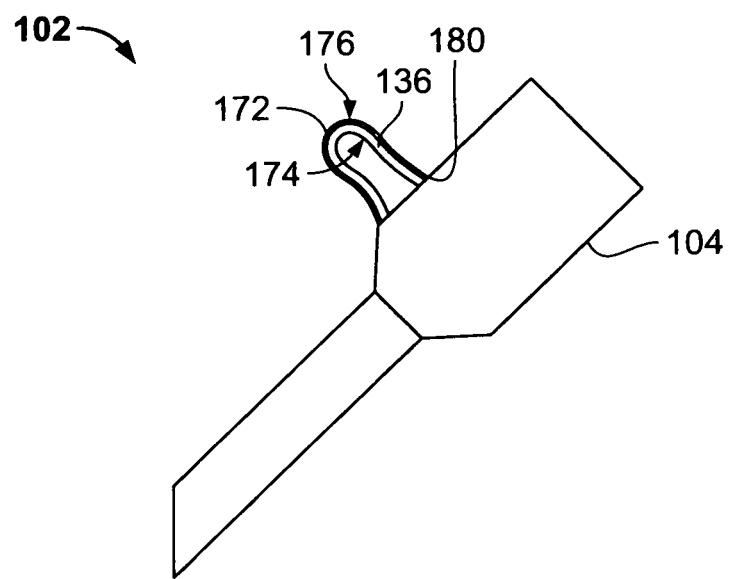
FIGS. 22-23 are illustrations showing two states of a trocar assembly with a cleaning element having a finger port.
Figure 23:
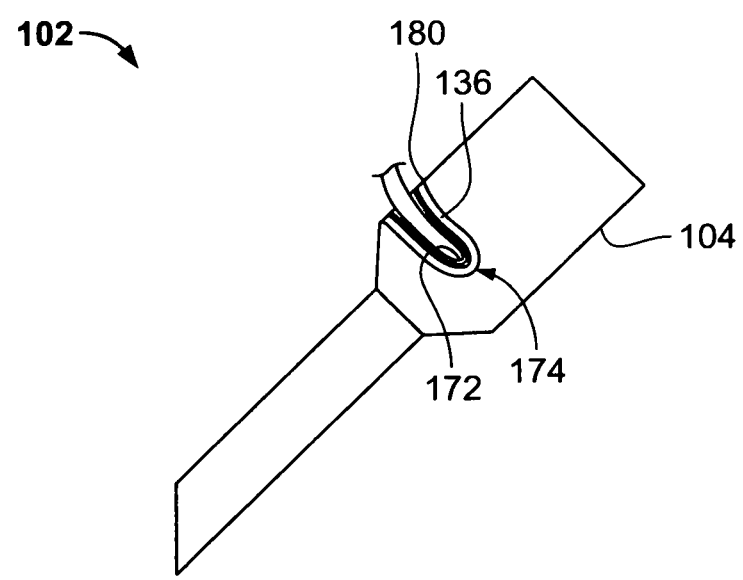

FIGS. 22-23 show an embodiment of a trocar assembly 102 with a cleaning port 172 configured to receive a finger of a user, where each drawing figure includes an external view and a cutaway view showing internal components. The cleaning port 172 may be substantially formed by a flexible portion (e.g., a rubber, flexible plastic, or another suitable material), and a cleaning element 136 may be located on an inner surface 174 of the cleaning port 172. The inner surface 174 may be the surface facing and exposed to the conditions of the interior of a housing 104. An exterior surface 176 may face outward with respect to the interior of the housing 104 and may have particular surface characteristics such that it is configured to contact and communicate one or more fingers of a user. The housing 104 may include an opening 181 aligned with the cleaning port 172 such that a finger can be inserted through the opening 181. During a cleaning procedure, the cleaning port 172 may be forced/directed through the opening 181 and into the interior of the housing 104 such that a scope can contact the cleaning element 136. Advantageously, the user (which may be a medical professional) may be capable of receiving haptic feedback on the finger(s) (i.e., feedback through perception through the sense of touch) to confirm that the cleaning element is being cleaned and/or is ready for re-deployment into a cannula. And, the user may be able to use the finger(s) to "scrub" one or more surfaces of the scope by moving the inner surface 174 relative to the scope, the scope relative to the inner surface, or both—with user-varied intensity and location of contact for removing material from the scope as desired. Further, since the cleaning port 172 may be substantially outside of the housing 104 in a default state (at least prior to the first cleaning procedure), the cleaning port 172 may be out of the way and prevented from restricting the medical procedure until it is needed. Optionally, the cleaning port 172 may have a tendency or bias to take on its default state (e.g., substantially outside of the housing 104) such that, when a finger releases from the cleaning port 172, the cleaning port 172 moves into its default state. The tendency or bias may be provided by material properties of the cleaning port 172 and/or by a separate element (e.g., a spring mechanically coupled to the cleaning port 172).

Figure 24:
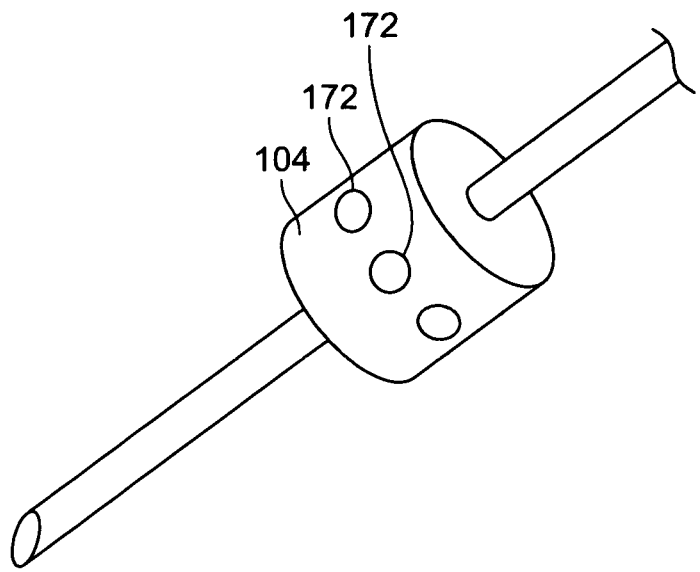
FIGS. 24-25 are illustrations showing various views of a trocar assembly with a cleaning element having a plurality of finger ports.
Figure 25:
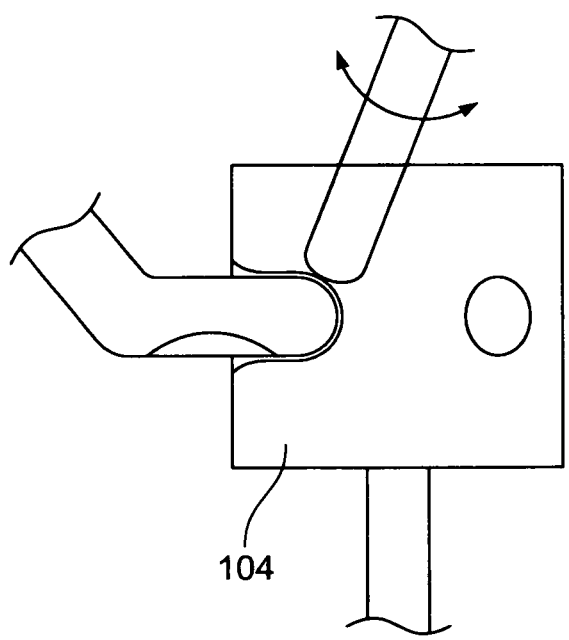

As shown in FIGS. 24-25, some embodiments may include a plurality of cleaning ports 172 in accordance with the cleaning portion with reference to FIG. 22-23. Such embodiments may include (as shown) elastic or otherwise flexible/extensible cleaning portion(s) that generally align with contours of the wall of the housing 104 in a default state as shown on the left/external view, but which may be deflected/extended into the internal volume of the housing 104 for cleaning in the manner described relative to FIGS. 22-23, where—when a plurality of such ports are present, the inward-facing surface of each may have different properties (e.g., a fine-grit surface, a coarse-grit surface, a polishing surface, and/or any combination of surface textures, cleaning materials, lubricants, or other features, each of which can also be used in other embodiments disclosed herein).

Figure 26:
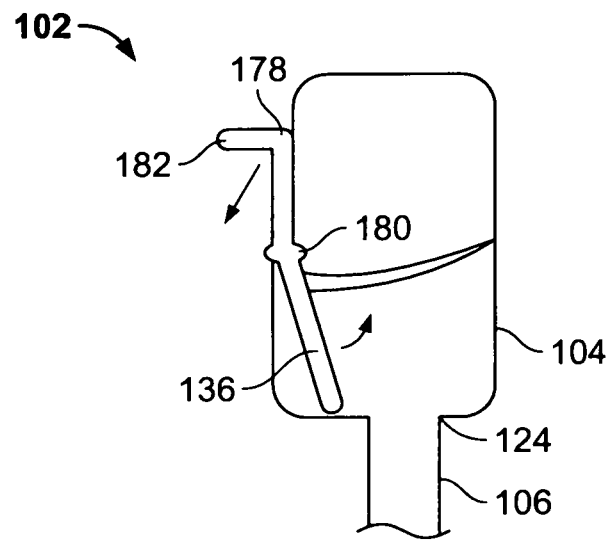
FIG. 26 is an illustration showing a trocar assembly having a cleaning element that is pivotable within a housing chamber.

FIG. 26 shows an embodiment of a trocar assembly 102 with a cleaning element 136 that is movable via actuation of a lever 178. A pivot 180 may be included at the location where the cleaning element 136 is connected to the lever 178, and the pivot 180 may be rotatably coupled to a wall of a housing 104 of the trocar assembly 102 (as depicted). Optionally, the cleaning element 136 may be coupled to a spring or another device that provides the cleaning element 136 with a tendency or bias to assume a default position where the cleaning element 136 does not obstruct an opening 124 leading to a cannula 106. When a user actuates the lever 178, the lever may cause rotation of the cleaning element 136 such that the cleaning element 136 moves into position for access by and/or contact with a scope such that the cleaning element 136 can contact (and clean) the scope. The lever 178 may include a handle/flap 182 that such that the lever 178 can be easily grabbed and/or gripped by a user even if the majority of the lever 178 is approximately flush with the wall of the housing 104.

Figure 27:
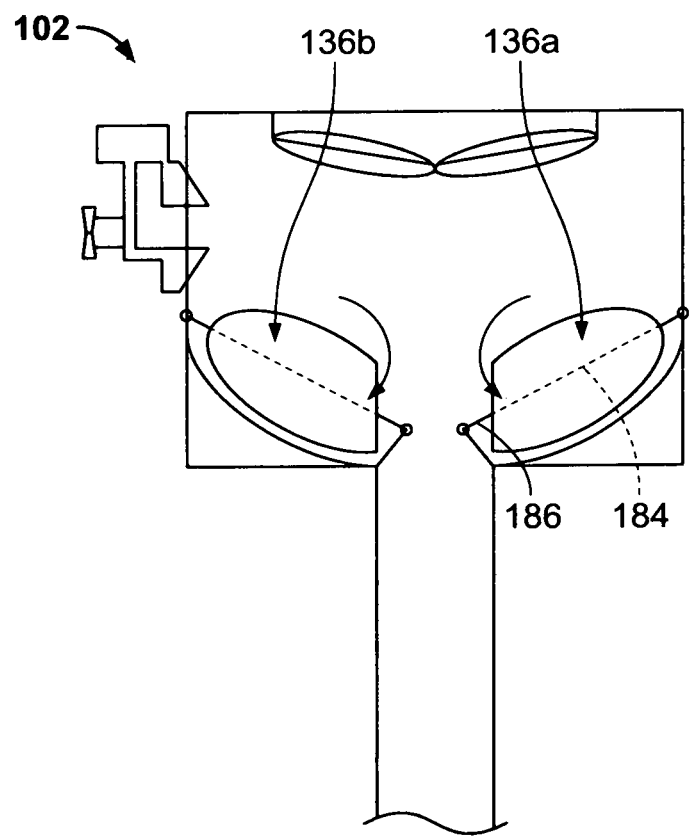
FIG. 27 is an illustration showing a trocar assembly having two cleaning elements, where each of the cleaning elements is rotatable about their respective longitudinal axes.

FIG. 27 shows a trocar assembly 102 having two cleaning elements 136a and 136b. Each of the cleaning elements 136 has an elongated body shape with a longitudinal axis 184, and each is rotatable along its longitudinal axis 184. Thus, the cleaning elements 136 may be rotatable when in contact with the distal end of a scope to provide a wiping effect to remove debris. Additionally or alternatively, the rotatable cleaning elements 136 may be advantageous since they can rotate a clean portion of the cleaning surface towards the scope after prior contact, which can prevent re-contaminating the distal end of the scope with substances that were previously removed from the scope.

To provide the ability to rotate, a pin 186 may extend through the cleaning elements 136. The cleaning elements 136 can be rotatable about the pin (thus preventing the need for the pin 186 itself to be rotatable), or the cleaning elements 136 can be fixed with respect to the pin 186 and the pin 186 itself can be rotatably-coupled to the remainder of the chamber (e.g., through a socket joint at each end). Further, while only two cleaning elements 136 are shown in FIG. 27, more (or less) can be provided with the same or similar structures.

Figure 28:
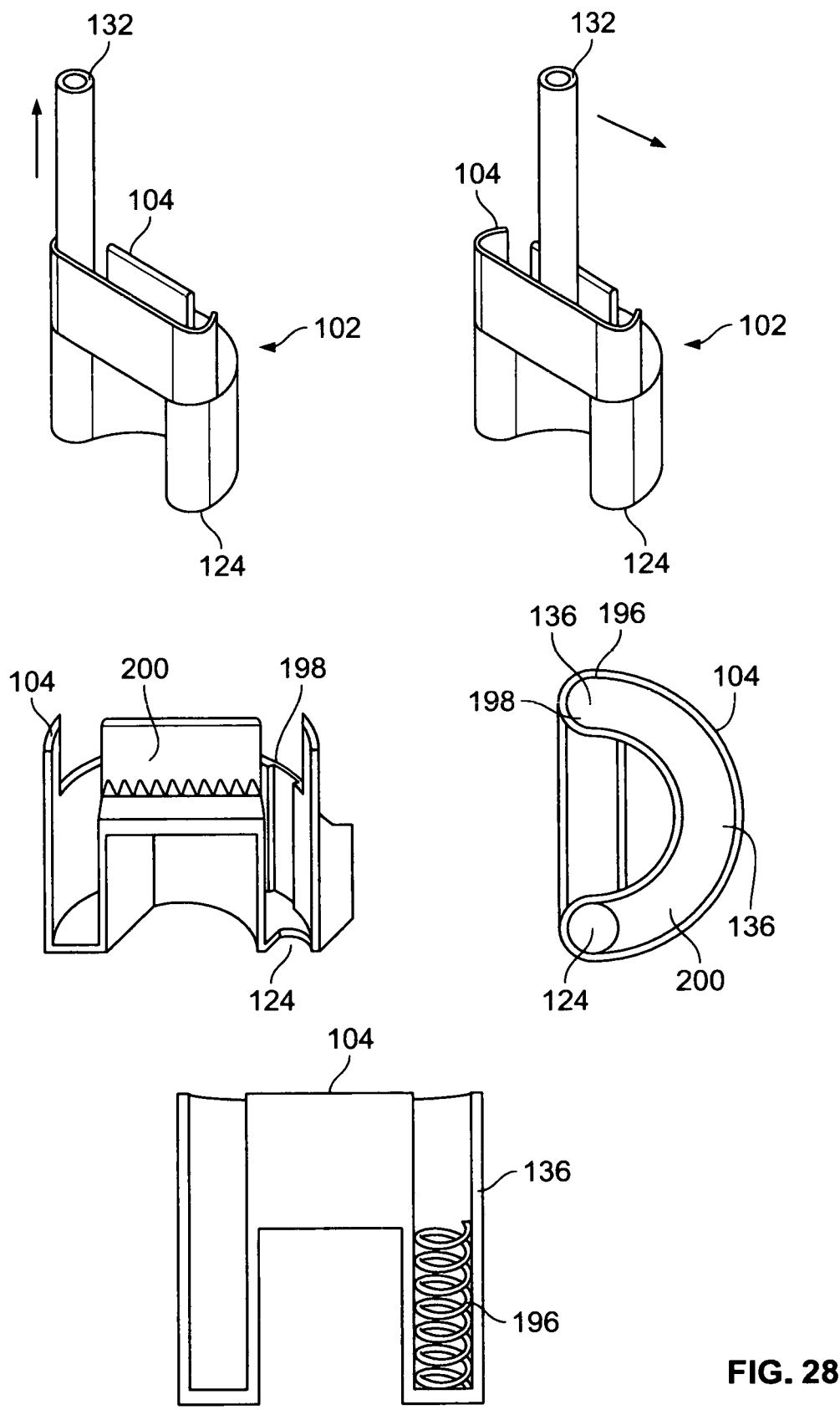
FIG. 28 is an illustration showing a trocar assembly having a track with multiple cleaning portions.

FIG. 28 shows several views of an embodiment of a trocar assembly 102 having a particular cleaning course or track for a scope 132, where a distal end of the scope 132 may move through the cleaning course in a particular sequence to ensure suitable cleaning. The cleaning course may have any suitable elements arranged in any suitable arrangement. In the embodiment depicted by FIG. 28, for example, the cleaning course includes a cleaning element 136 having a spiral brush design 196 located within a cavity 198 of a housing 104. The cleaning element 136 may further include a ribbed channel 200 that extends from the cavity 198 to an opening 124 (where the opening 124 may extend to a cannula 106). The spiral brush design 196 of the cleaning element 136 may have a plurality of bristles formed with particular characteristics (e.g., a particular size, position, compliance, absorbance tendency, etc.) such that the bristles remove most debris from the scope 132 (analogous to a "rough cleaning"). After a scope is cleaned by the spiral brush design 196, it may be moved across the ribbed channel 200 for additional cleaning or polishing (analogous to a "fine cleaning"). In combination, the spiral brush design 196 and the cavity 198 may provide a suitable level of cleaning of a scope in a quick and efficient matter, and the shape of the housing 104 may be laid out to provide guidance to the medical professional such that the desirable cleaning sequence is easily discernable by looking at the shape of the housing 104.

Figure 29:
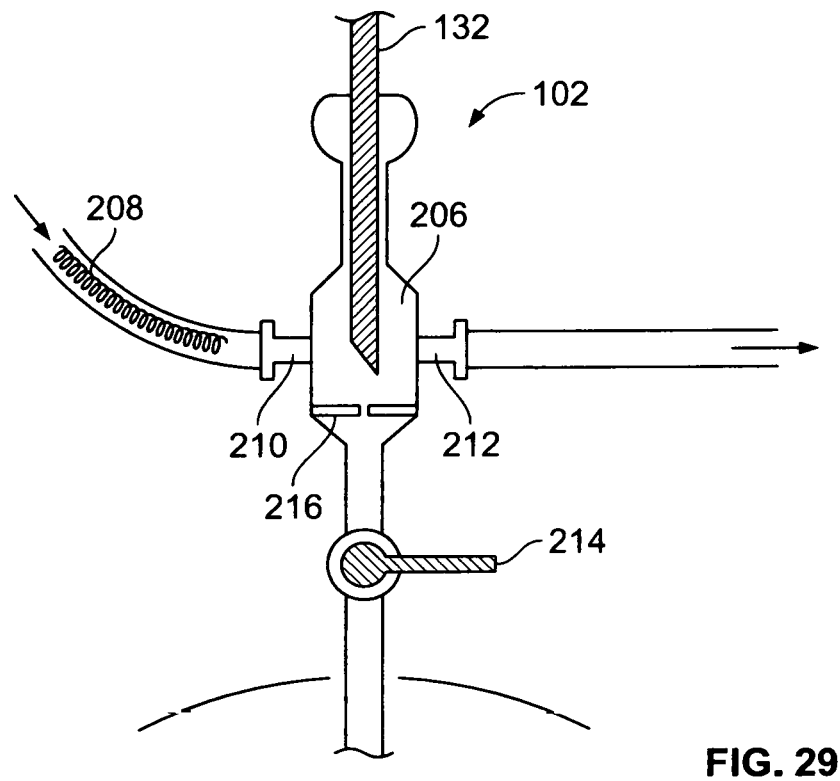
FIG. 29 is an illustration showing a trocar assembly having a flushing chamber, where the flushing chamber is associated with an inlet and an outlet.

As shown in FIG. 29, the trocar assembly 102 may include a flushing chamber 206. The flushing chamber 206 may be included in addition to, or as an alternative to, the solid cleaning elements described above. For example, the flushing chamber 206 may be located distally within a trocar depicted by any of FIG. 1-28. Referring to FIG. 29, to clean the distal end of the scope 132, the distal end of the scope 132 may be inserted into the flushing chamber and held in place while a cleaning agent 208 flows from an inlet 210 to an outlet 212. The cleaning agent, which may include a fluid (e.g., water, saline, and/or any suitable chemical agent dissolving or washing away the obstructions), may continuously flow from the inlet 210 to the outlet 212, or it may alternatively be controlled through a valve or by starting/stopping a pump or other device controlling the flow rate. The cleaning agent may be heated, but heating is not required in all embodiments. In some instances, more than one type of cleaning agent 208 may be used in sequential steps (e.g., a first agent may target a certain type of obstruction, while a second agent used later may target another type). While the cleaning agent will typically be a liquid, additionally or alternatively, a gas (rather than liquid) may flow through the chamber, particularly when a drying step is desirable.

To prevent the cleaning agent from entering the body of a patient through the trocar, a valve 214 may be included (although it may not be necessary when body-compatible cleaning agents are used, such as saline). The valve 214 may be closed during the flow of the cleaning agent and then opened later to provide the scope with access to the trocar's distal end (now shown) and the treatment location within the body. Additionally or alternatively, a flap 216 of fabric, rubber, and/or another material may be located distally of the flushing chamber 206. The flap 216 may act as a secondary valve (or may replace the valve 214 altogether). The flap 216 may provide a surface for wiping and/or drying the distal end of the scope 132 to wipe away any remaining obstructions and remove the cleaning agent.

Figure 30:
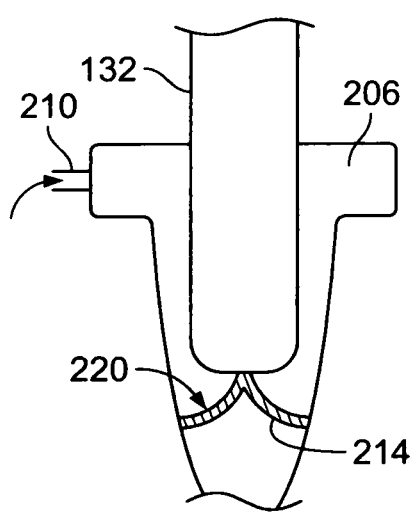
FIG. 30 is an illustration showing an inverted duckbill valve for a flushing chamber of a trocar assembly.

As an alternative to, or in addition to, the flap 216 and/or the valve 214, an inverted duckbill seal 218 may be included (as shown in FIG. 30). The inverted duckbill seal 218 may include surface(s) 220 that are configured to deform as the scope 132 is pressed through distally. As the surfaces 220 deform (e.g., to allow the scope 132 through), they may rub against and clean the distal end of the scope 132 (e.g., in a similar manner to the cleaning elements described above). The inverted duckbill seal 218 may also function to prevent a fluid cleaning agent from leaking distally through the flushing chamber 206. The sealing properties of the inverted duckbill seal 218 may be retained both when (1) the distal end of the scope 132 is in the flushing chamber 206 (as shown in FIG. 30), and also (2) when the distal end of the scope 132 is located distally of the inverted duckbill seal 218. Thus, the inverted duckbill seal 218 may be advantageous for preventing the need of including a valve (e.g., the valve 214 of FIG. 29) which must be manually opened or closed. The inverted duckbill seal 218 may also provide an additional measure of safety when the valve 214 is included, particularly when the fluid used in the flushing chamber 206 should not enter the body.

One difference between the depicted embodiment of FIG. 30 and the depicted embodiment of FIG. 29 is that the embodiment of FIG. 30 excludes an outlet, but rather only an inlet 210 is included. This embodiment may be advantageous where the cleaning agent is compatible with the body, such as when the cleaning agent is a saline. In other embodiments, the inlet 210 may provide access to the scope with another device, such as an external cleaning device (not shown) that is inserted through the inlet 210. For example, an elongated instrument may be inserted through the inlet 210 to wipe contaminants and/or obstructions from the surface of a scope. It is also contemplated that a vacuum may be formed through the inlet 210 to remove a cleaning agent after flushing.

Figure 31:
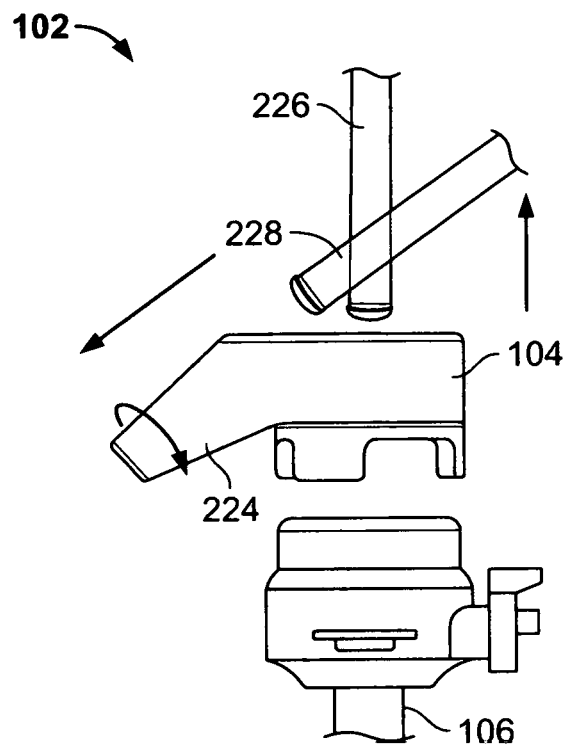
FIGS. 31-32 are illustrations showing various views of a trocar assembly having an offshoot for cleaning a scope.
Figure 32:
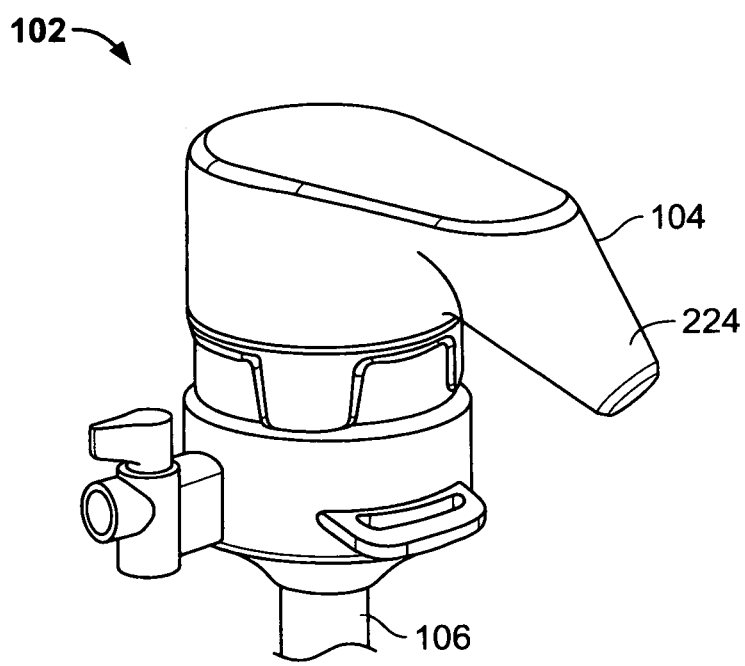

FIGS. 31-32 show an embodiment of a trocar assembly 102 having an offshoot recess 224 for cleaning a scope. The offshoot 224 may include a cleaning element, which may incorporate any of the features related to any of the cleaning elements described herein. For example, the cleaning element may be located within the offshoot 224 and may incorporate bristles, one or more pads of absorbent material, a movable cleaning surface, etc. As illustrated in FIG. 31, when a scope has a first orientation 226, it may be aligned with the cannula 106 such that, when moved distally along its longitudinal axis, a distal end of the scope is deployed through the cannula 106. When oriented in a second orientation 228, the scope may be aligned with the offshoot 224 such that, when moved along its longitudinal axis, the distal end of the scope enters the offshoot 224 for cleaning. Once in the offshoot 224, the scope may be rotated and/or repeatedly moved such that the distal end of the scope contacts or otherwise communicates with a cleaning element in the offshoot 224 during a cleaning process. The housing 104 may be shaped and sized such that there is suitable room for a change in orientation of the scope from the first orientation 226 to the second orientation 228. The top of the housing 104 may be coupled to a flexible valve or seal (such as the depicted duckbill seal shown in FIG. 1) which allows a change in the orientation of the scope without compromising the closed environment within the housing 104. Advantageously, the cleaning element within the offshoot 224 may be accessed when desired by a medical professional but may remain out of the way and unobstructive with respect to the cannula 106. It is contemplated that the offshoot 224 may be accessible such that the cleaning element within the offshoot 224 can be replaced or reprocessed when soiled.

FIG. 33 shows another embodiment of a trocar assembly 102 having an offset 224. The offset 224 may include a cleaning agent 208 (e.g., a fluid), which may include a liquid, a gel, or other material for dissolving or washing away obstructions, residues, etc. The offset 224 may be used in a trocar assembly in addition to any other cleaning elements, flushing chambers, or the like described herein. For example, it is contemplated that the offset 224 may be associated with a flushing chamber (that is, the flushing chamber may be located in the offset 224) such that the flushing chamber does not interfere with access by the scope to the distal end of the trocar.

In some embodiments, offshoots may have replaceable cleaning elements. For example, referring to FIG. 34 (showing an embodiment of a trocar assembly 102 with an offshoot 224 and a cleaning element 136), the cleaning element 136 may include removable tabs 230 that are accessible/removable by a user. Each of the removable tabs 230 may include a cleaning surface 135 facing the chamber of the housing 104. The cleaning surface 135 may incorporate any of the features with respect to any of the cleaning surfaces/cleaning elements described herein. An exposed tab of the removable tabs 230 may be initially used to clean a scope within the offshoot 224. Once soiled or otherwise compromised (e.g., due to scope cleaning), the top tab may be pulled out of the offshoot 224 and discarded (or reprocessed), while those of skill in the art will appreciate that the offshoot may include one or more structures for auto-advancing "the next tab(s) in line" toward the chamber for use in cleaning/wiping a scope. Advantageously, the availability of multiple removable tabs 230 may ensure that a fresh and non-compromised cleaning surface is available for an extended period of time and/or over multiple scope-cleaning steps.

Figure 36:
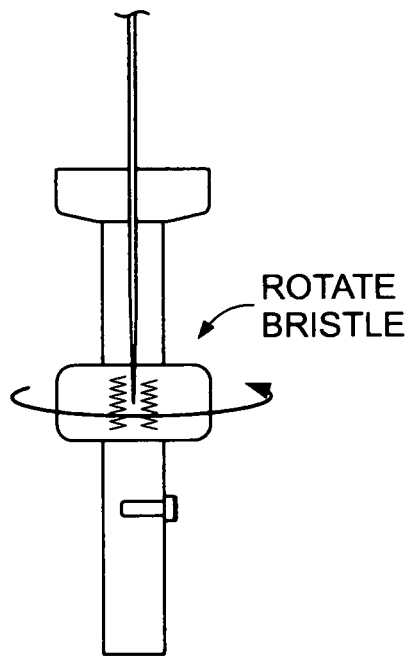
Figure 37:
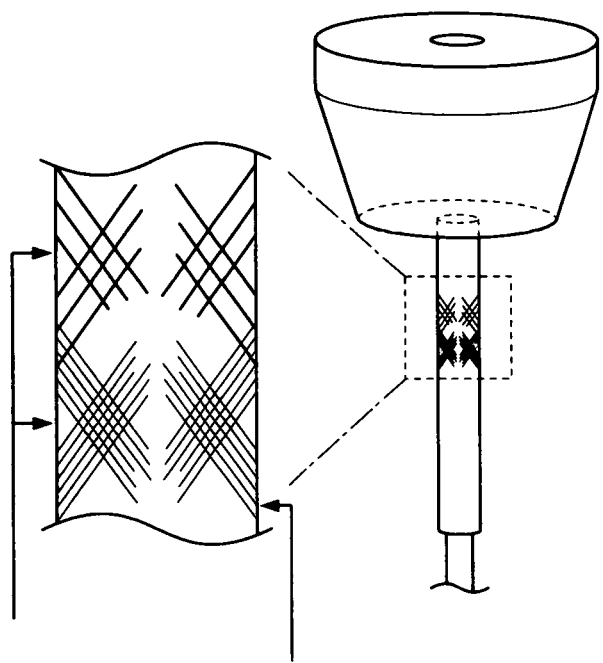
Figure 38:
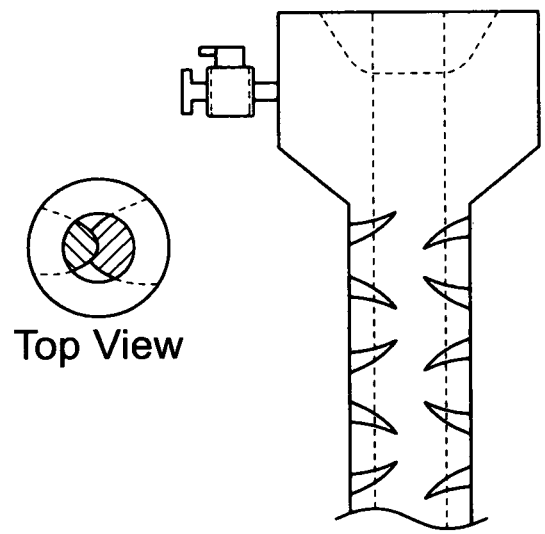

Bristles with other orientations, sizes, locations, and/or materials may be additionally or alternatively used. FIGS. 35-38 show four different embodiments of trocar assemblies with bristles for purposes of non-limiting illustration. FIG. 35 illustrates a set of bristles that may be located in a chamber along the length of a cannula (but not necessarily at a distal end). FIG. 36 shows a set of bristles located along the cannula in a rotatable member, which may be advantageous where it is desirable to achieve relatively rotation between the bristles and the scope without rotating the scope itself (e.g., if the scope is connected to wires or other objects that may complicate its rotation). FIG. 37 shows bristles that have different orientations (e.g., certain bristles are angled proximally with respect to perpendicular to the longitudinal axis of the cannula and others are angled distally). Other suitable angles or other orientations may additionally or alternatively be used. FIG. 38 shows relatively robust bristles that are spaced along the length of the cannula. In some embodiments (not shown), bristles of different sizes may be used at different locations (e.g., robust bristles may be used for "rough cleaning" and smaller bristles may be used for "fine cleaning" and/or polishing).

Figure 39:
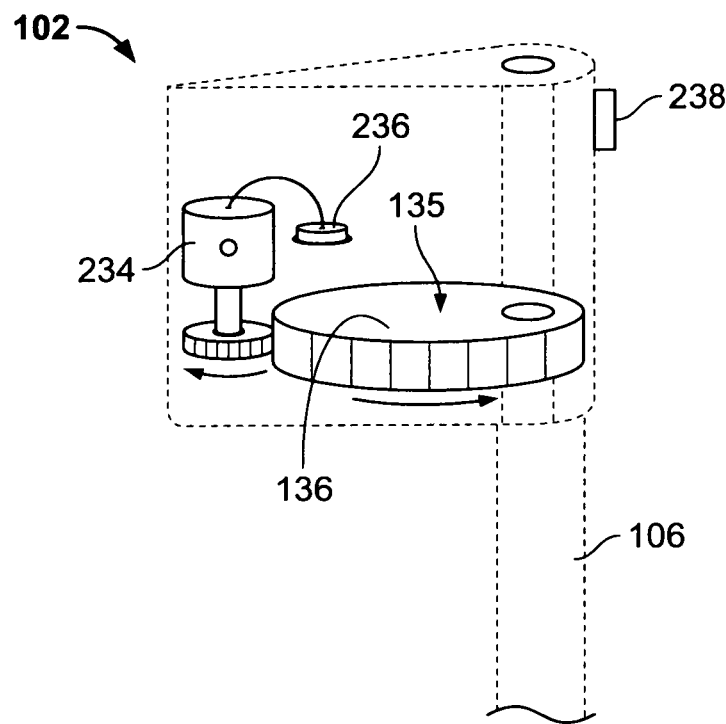
FIG. 39 is an illustration showing a trocar assembly with a motorized cleaning element.

Each of the embodiments described above having a movable component, such as a movable cleaning element, a movable valve, etc., may include a suitable actuator for providing the movement. If an actuator is included, it may be manually operated (e.g., through pushing a button) and/or it may be operated by a computer or other programmed processor. For example, referring to FIG. 39, a trocar assembly 102 includes a movable cleaning element 136 (in this case a rotatable cleaning element). As shown, a motor 234 is included for causing movement of the cleaning element 136. The motor 234 may be coupled to a power source, such as a battery 236, and a button 238 or other actuation interface may be included. In this particular embodiment, it is contemplated that the motor 234 may continuously spin the cleaning element during an active mode (or "on" mode) to provide automatic brushing/cleaning when a scope contacts the top surface 135 of the cleaning element 136. In other embodiments, a motor or other actuator may function to simply move the cleaning element from one state to another.

Figure 40:
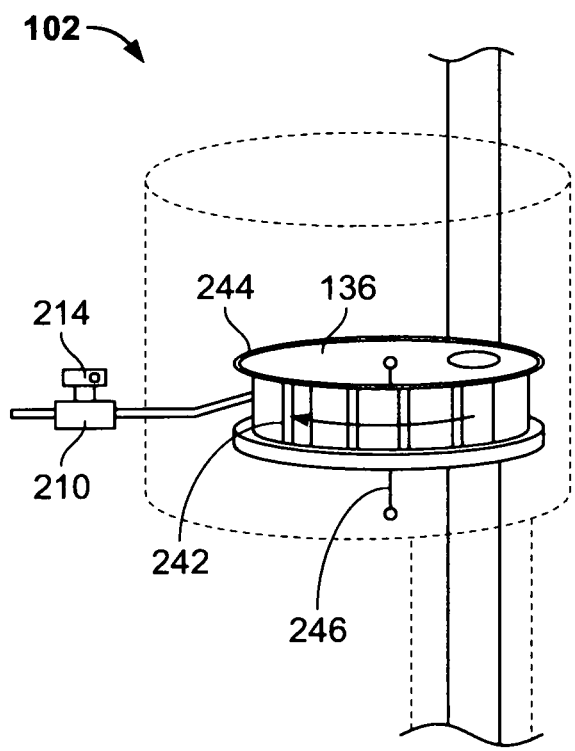
FIG. 40 is an illustration showing a trocar assembly having a cleaning element that is movable through actuation of an insufflation inlet.

Another example of an actuator for moving a cleaning element, applicable to all embodiments herein, is an insufflation inlet 210 included with a trocar assembly 102 shown in FIG. 40. As shown, the insufflation inlet 210 may direct pressurized fluid (e.g., insufflation gas) towards a cleaning element 136, and particularly towards blades 242 located on a side 244 of the cleaning element 136. The cleaning element 136 may be pivotable about its center axis (and/or about a pivot pin 246) such that the cleaning element 136 moves when the pressurized fluid is released from the insufflation inlet 210. When movement of the cleaning element 136 is not desired, the insufflation inlet 210 can be directed away from the cleaning element 136 (e.g., without turning off the insufflation inlet 210), or pressure provided at the insufflation inlet 210 can simply be stopped (e.g., through operating a valve 214). While the motor 234 of FIG. 39 and the insufflation inlet 210 of FIG. 40 are included as exemplary examples of actuators for moving a cleaning element, any other suitable actuator can be used (e.g., hydraulic devices, piezoelectric actuators, comb drives, servomechanisms, or the like).

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. This specifically includes that the structure, location, and mechanisms of the disclosed cleaning elements and related structures in the different embodiments illustrated and described with reference to the drawing figures may be combined and elements interchanged within the level of skill in the art as informed by this application, and within the scope of the present claims, which includes that a variety of disclosed individual cleaning element components dimensioned for use encompassed within in laparoscopy trocars may be configured as separable/replaceable components of a larger trocar assembly. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment.

In the event of any inconsistent disclosure or definition from the present application conflicting with any document incorporated by reference, the disclosure or definition herein shall be deemed to prevail.

We claim:

1. A trocar assembly with an integrated scope-cleaning structure, the trocar assembly comprising:
   a proximal portion configured for accessibility by a user;
   a cannula extending distally from the proximal portion and configured to extend distally into a patient body, wherein the cannula is further configured to receive a distal end of a scope such that the scope can be maneuvered through the cannula to a location within the patient body; and
   a cleaning element,
   wherein the proximal portion includes a housing,
   wherein the cleaning element is substantially located within the housing, and
   wherein the cleaning element includes an operation surface actuatable from outside of the housing and operatively linked to the cleaning element through a sidewall of the housing such that actuation of the operation surface relative to the housing moves the cleaning element within the housing without a scope in the housing.

2. The trocar assembly of claim 1, wherein the cleaning element is rotatable between a first state and a second state, wherein in the first state, a gap of the cleaning element is aligned with an opening of the housing, and wherein in the second state, the cleaning element obstructs the opening of the housing.

3. The trocar assembly of claim 2, wherein the opening of the housing is located at a proximal end of the cannula.

4. The trocar assembly of claim 2, wherein the cleaning element includes a second gap that is selectively alignable with a second opening of the housing.

5. The trocar assembly of claim 2, wherein the cleaning element includes an outer surface and an inner surface, wherein each of the outer surface and the inner surface are configured for cleaning a distal end of a scope.

6. The trocar assembly of claim 1, wherein the cleaning element includes a collapsible portion that is offset with respect to a distal opening when in a default state.

7. The trocar assembly of claim 1, wherein the cleaning element includes at least one door that is pivotable about a hinge.

8. The trocar assembly of claim 1, wherein the cleaning element includes an elongated shape with a longitudinal axis, and wherein the cleaning element is rotatable about the longitudinal axis.

9. The trocar assembly of claim 1, wherein the housing has an opening for receiving a finger port, and wherein the finger port with an inner surface comprising the cleaning element.

10. The trocar assembly of claim 1, further comprising a flushing chamber located distally of the cleaning element, the flushing chamber being in fluid communication with an inlet configured to supply the flushing chamber with a fluid cleaning agent.

11. A trocar assembly with an integrated scope-cleaning structure, the trocar assembly comprising:
    a proximal portion;
    a cannula extending distally from the proximal portion and configured to extend distally into a patient body, wherein the cannula is further configured to receive a distal end of a scope such that the scope can be maneuvered through the cannula to a location within the patient body; and
    a cleaning element,
    wherein the proximal portion includes a housing,
    wherein the cleaning element is located within the housing, and
    wherein the cleaning element is coupled to an actuator that rotates the cleaning element within the housing when actuated.

12. The trocar assembly of claim 11, wherein the actuator includes a torsion spring.

13. The trocar assembly of claim 12, wherein an actuation interface is coupled to the torsion spring, wherein the actuation interface is accessible from outside the housing, and wherein the actuation interface is configured to activate the torsion spring to move the cleaning element.

14. The trocar assembly of claim 11, wherein the actuator includes a motor.

15. The trocar assembly of claim 11, wherein the actuator includes a insufflation inlet, and wherein the insufflation inlet is configured to direct pressurized gas towards a blade of the cleaning element.

16. A trocar assembly with an integrated scope-cleaning structure, the trocar assembly comprising:
    a cannula configured to extend distally into a patient body, wherein the cannula is further configured to receive a distal end of the scope such that the scope can be maneuvered through the cannula to a location within the patient body;
    a housing comprising a flushing chamber positioned proximally of at least a portion of the cannula and configured to receive a distal end of a scope;
    an inlet for supplying a fluid cleaning agent to the flushing chamber;
    an outlet spaced from the inlet, the outlet in fluid communication with the flushing chamber for directing the fluid cleaning agent to a location outside the flushing chamber; and
    a cleaning element located in the housing, the cleaning element includes an operation surface that is actuatable from outside the housing an operatively linked to the cleaning element through a sidewall of the housing such that actuation of the operation surface relative to the housing moves the cleaning element within the housing without a scope in the housing.

17. The trocar assembly of claim 16, further comprising a valve located distally of the flushing chamber.

18. The trocar assembly of claim 17, wherein the valve is an inverted duckbill valve.

19. The trocar assembly of claim 16, wherein the flushing chamber is located in an offshoot from the cannula.

* * * * *